(12) United States Patent
Jung et al.

(10) Patent No.: US 6,689,890 B2
(45) Date of Patent: Feb. 10, 2004

(54) EFFICIENT LACTAM SYNTHESIS

(75) Inventors: Kyung Woon Jung, Tampa, FL (US); Cheol Hwan Yoon, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/323,537

(22) Filed: Dec. 18, 2002

(65) Prior Publication Data

US 2003/0171599 A1 Sep. 11, 2003

Related U.S. Application Data

(63) Continuation-in-part of application No. 09/848,268, filed on May 4, 2001, now abandoned.
(60) Provisional application No. 60/201,734, filed on May 4, 2000.

(51) Int. Cl.$^7$ ............................................. C07D 207/12
(52) U.S. Cl. ..................................................... 548/544
(58) Field of Search ......................................... 548/544

(56) References Cited

FOREIGN PATENT DOCUMENTS

WO  WO 98 50344 A  11/1998

OTHER PUBLICATIONS

Dicosimo et al., "Chemoenzymatic Production of Lactams from Aliphatic α,ω–Dinitriles", *J. Org. Chem.* (1998), 63:4792.
Meyers et al., "Asymmetric Synthesis of γ, γ–aminobutyric Acid Analogues and 2,2–Disubstituted Pyrrolidines", *J. Am. Chem. Soc.* (1991), 113: 9858.
Salvatore et al., "Cesium Hydroxide Promoted Chemoselective N–Alkylation for the Generally Efficient Synthesis of Secondary Amines", *Org. Lett.* (1999), 1:1893.
Mateo et al., "Stereocontrolled Synthesis of 4–Substituted Kanaic Acid", *J. Org. Chem.* (1998), 63: 1995.
Wee et al., "Dirhodium Tetraacetate Catalyzed Carbon–Hydrogen Insertion Reaction in N–Substituted α–Carbomethoxy–α–diazoacetanilides and Structural Analogues. Substituent and Conformational Effects", *J. Org. Chem.* (1992), 57(16): 4404–4414.
Wee et al., "Metal–Catalyzed Reaction of Indoline Diazoamides Possessing a C–2 CH2X Substituent: Site–Selectivity, Diastereoselectivity, and Chemoselectivity", *J. Org. Chem.* (1996), 61(8): 2897–2900.
Pawda et al., "An Isomuenchone–Based Method for the Synthesis of Highly Substituted 2(1H)–Pyridones", *J. Org. Chem.* (1999), 64(23): 8648–8659.

Miah et al., "Ligand Effects in the Rhodium (ii) Catalysed Reactions of Diazoamides and Diazoimides", *Tetrahedron*, Elsevier Science Publishers, Amsterdam, NL (1996), 52(7): 2489–2514.
Doyle et al., "Synthesis of pyrrolizidine bases by highly diastereoselective and regioselective catalytic carbon–hydrogen insertion reactions of chiral pyrrolidinediazacetamides", *Tetrahedon Letters*, Elsevier Science Publishers, Amsterdam, NL (1996), 37(9): 1371–1374.
Sheehan et al., *J. Org. Chem.* (1997), 62: 438–439.
Wee et al., *J. Org. Chem.* (1999), 64: 8648–8659.
Yoon, Cheol Hwan, Michael J. Zaworotko, Brian Moulton, Kyung Woon Jung, Regio– and Stereocontrol Elements in Rh(11)–Catalyzed Intramolecular C–H Insertion of α–Diazo–α–(phenylsulfonyl)–acelamides, Organic Letters 3(22):3539–3542 (2001).
Yoon, Cheol Hwan, David L. Flanigan, Byong–Don Chong, Kyung Woon Jung, A Novel Synthetic Route to Chiral Y–Lactams from α–Amino Acids via Rh–Catalyzed Intramolecular C–H Insertion J. Org. Chem. 67:6582–6584 (2002).
Yoon, Cheol Hwan, Advait Nagle, Chiliu Chen, Drashti Gandhi, Kyung Woon Jung "Y–Lactam Synthesis via C–H Insertion: Elaboration of N–Benzyl Protecting Groups for High Regioselectivity toward the Total Synthesis of Rolipram" Organic Letters 5(13):2259–2262 (2003).

*Primary Examiner*—Bruck Kifle
(74) *Attorney, Agent, or Firm*—Saliwanchik, Lloyd & Saliwanchik

(57) ABSTRACT

Lactams, libraries of lactams, and an efficient method of synthesizing a lactam, including a γ-lactam, in which an α-diazoacetamide of the general structure (I) is reacted under conditions promoting intramolecular C—H insertion, for example in the presence of a rhodium salt such as $Rh_2(OAc)_4$,

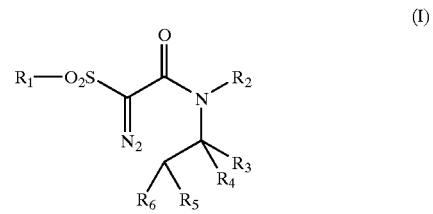

(I)

by which means lactams that are precursors in the synthesis of diverse natural and synthetic products, including pyrrolidinone compounds such as lactacystin, pramanicin, kainic acid, statine, AHPPA, and rolipram, are produced.

7 Claims, 1 Drawing Sheet

EFFICIENT LACTAM SYNTHESIS

RELATED APPLICATIONS

This application is a continuation-in-part application filed from U.S. Ser. No. 09/848,268; filed May 4, 2001 now abandoned and claims the benefit of provisional patent application Serial No. 60/201,734; filed May 4, 2000, which is incorporated by reference herein in its entirely, including any figures, tables, or drawings.

FIELD OF THE INVENTION

The present invention relates generally to synthetic methods for the preparation of lactams. More particularly, the present invention relates to efficient and economic synthetic methods for the preparation of optionally substituted lactams by intramolecular C—H insertion reactions of α-diazoamides, in which the α-diazoamides are activated for intramolecular C—H insertion, for example by sulfone substitution, and to compounds and libraries of compounds derived therefrom.

BACKGROUND OF THE INVENTION

Lactacystin, an exemplary chiral pyrrolidinone, possesses structural motifs common to a number of biologically active natural products such as kainic acid and epolactaene. These molecules, or their synthetic precursors, contain lactam cores (specifically, γ-lactam cores) that are highly functionalized. Numerous medicinal applications of such γ-lactam systems are known, encompassing applications as diverse as, for example, anticancer agents, psychotropic agents, neuromuscular transmission blockers, immunoregulators, neurological excitants, protease inhibitors, and antidepressants. Therefore, a general, efficient and economic synthesis of such chiral pyrrolidinones would facilitate ongoing and future health related research.

The pyrrolidinone functionality is a prevalent theme in various syntheses, and serves as a crucial intermediate in the synthesis of numerous natural products. Although a large number of synthetic methods have been reported to date (see, for example, DiCosimo, R., Gavagan, J. E., Fager, S. K., Fallon, R. D., Folsom, P. W., Herkes, F. E., Eisenberg, A., and Hann, E. C. "Chemoenzymatic Production of Lactams from Aliphatic α,ω-Dinitriles" 1998, J. Org. Chem. 63:4792), the reported asymmetric syntheses are inefficient, lengthy, and costly (see, for example, Meyers, A. I. and Burgess, L. E. "Asymmetric Synthesis of γ,γ-Dialkyl-γ-aminobutyric Acid Analogues and 2,2-Disubstituted Pyrrolidines" 1991, J. Am. Chem. Soc. 113:9858 ).

Due to their biological activities and interesting structural features, it is also desirable to develop improved synthesis of lactacystin and clasto-lactacystin β-lactone. New methodology for the construction of the lactam core in order to carry out targeted synthesis efficiently is also desirable.

For example, the biological activity of lactacystin and clasto-lactacystin β-lactone (FIG. 1), is relevant to the regulation of apoptosis, an active research area for the development of anti-cancer treatments. The process of apoptosis (programmed cell death), which is regulated by the oncoprotein Bcl-2, is targeted through the inhibition of the 20S proteasome, which overcomes the Bcl-2 protective function and thereby induce cell death. Thus, specific inhibition of the 20S proteasome has been proposed for the selective destruction of cancerous cells but not normal cells. As a well-known specific inhibitor of the targeted proteasome, lactacystin has attracted considerable attention from synthetic chemists. Lactacystin is a natural product obtained from microbial metabolites, which induces neurite outgrowth in neuroblastoma cells as well as inhibits progression of human osteosarcoma cells. This natural product and its analog, clasto-lactacystin β-lactone, also induce apoptosis in human monoblast cells. Because of scarcity and significant bioactivity, there is a need for economic total syntheses of these chiral pyrrolidinone compounds.

For synthesis of such chiral pyrrolidinones, amino acids are potential versatile starting materials. To effect the chiral pyrrolidinone synthesis, these amino acids require a ring closure reaction. In one approach, initramolecular C—H insertion reactions of α-diazoamide are used, catalyzed by rhodium salts. However, α-diazoamides are poor substrates in ring closures through C—H insertions, mainly due to competing side reactions, poor regioselectivities, and poor stereoselectivities (Table 1).

| $R^1$ | $R^2$ | Z | Yield (7:8) |
|---|---|---|---|
| $^i$Pr | $^i$Pr | $CH_3CO$ | 89% (>99:<1) |
| $^i$Pr | $^i$Pr | H | 95% (81:19) |
| $^i$Bu | $^i$Bu | $CH_3CO$ | 92% (37:63) |
| $^i$Bu | $^i$Bu | H | 95% (<1:>99) |
| PMP | $^i$Bu | $CO_2Me$ | 76% (8:92) |
| $^i$Bu | $PhCH_2CH_2$ | $CH_3CO$ | 94% (49:51) |
| $^i$Bu | $PhCH_2CH_2$ | H | 85% (<1:32) |
| PMP | $PhCH_2CH_2$ | $CO_2Me$ | 84% (<1:>99) |
| $^i$Pr | $^i$Pr | $CH_3CO$ | 89% (>99:<1) |
| $^i$Pr | $^i$Pr | H | 95% (81:19) |
| $^i$Bu | $^i$Bu | $CH_3CO$ | 92% (37:63) |
| $^i$Bu | $^i$Bu | H | 95% (<1:>99) |
| PMP | $^i$Bu | $CO_2Me$ | 76% (8:92) |
| $^i$Bu | $PhCH_2CH_2$ | $CH_3CO$ | 94% (49:51) |
| $^i$Bu | $PhCH_2CH_2$ | H | 85% (<1:32) |
| PMP | $PhCH_2CH_2$ | $CO_2Me$ | 84% (<1:>99) |

Common alternative methods employ the use of α-diazoacetamides, α-diazoacetoacetamides, and α-diaomalonamides, which also give rise to regiochemical mixtures. Such reactions are performed at elevated temperature, and often provide low diastereoselectivities. Thus, each reaction gives poor yields and/or a complicated mixture of products, as illustrated below in Scheme A:

Scheme A

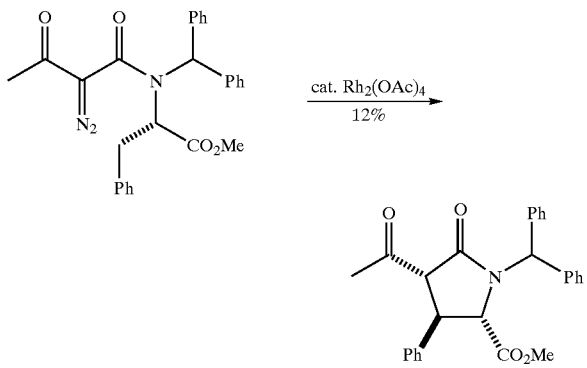

Zarogoza, F. J. Prakt. Chem., 1995, 292.

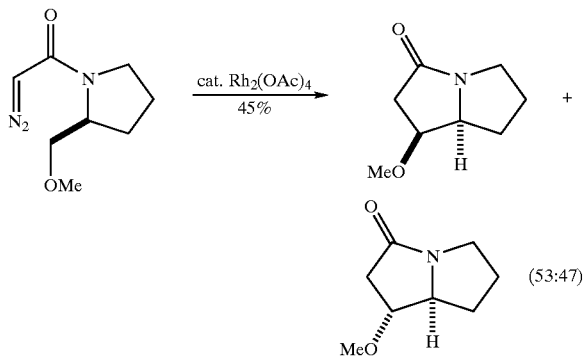

Doyle, M. P. Tetrahedron Lett., 1996, 37, 1371.

It is a further object of the prevent invention to provide a means for synthesis bioactive compounds including, but not limited to, pramanicin, statine, AHPPA, kainic acid, rolipram, and eoplactaene.

The above and other features and advantages are achieved through the use of a novel synthetic method as herein disclosed. In accordance with one embodiment of the present invention, there is provided a method of synthesizing a lactam, the method comprising firstly providing an α-diazoacetamide of structure (I),

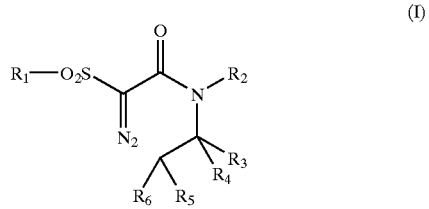

(I)

in which $R_{1-6}$ are substituents that can include H, halo, $N_3$, CN, NC, $(C_1-C_{22})$alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$aralkyl, $(C_7-C_{32})$alkylaryl, $(C_9-C_{32})$aralkenyl, $(C_9-C_{32})$alkenylaryl, OR, SR, $N(R)_2$, NH(R), $CO_2R$, C(O)R, $P(O)(OR)_2$, COR, $CF_3$, S(O)R, or $SO_2R$, wherein each R is independently H, $(C_1-C_{22})$alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$aralkyl, $(C_7-C_{32})$alkylaryl, $(C_9-C_{32})$aralkenyl, or $(C_9-C_{32})$alkenylaryl; or $R_2$ and $R_3$ together comprise $(C_1-C_{22})$alkyl, $(C_2-C_{22})$alkenyl, $(C_7-C_{32})$alkylaryl, $(C_9-C_{32})$alkenylaryl, —C(CH_3)_2—O—CH_2—, —(CH_2)_n—O—C(O)—, —C(X)—O—CH_2— or —C(X)—CH_2—O—, where n=0–10, and X is $(C_6-C_{10})$aryl or $(C_7-C_{32})$alkylaryl.

Secondly, the α-diazoacetamide is reacted under conditions that promote intramolecular C—H insertion, whereby a lactam is synthesized.

In accordance with another embodiment of the present invention, lactams synthesized by the foregoing method are provided. An exemplary lactam compound synthesized according to the method of the present invention is clasto-lactacystin β-lactone.

In accordance with another embodiment of the present invention, a library of lactams synthesized by the foregoing method is provided, where such a library may be used, for example, in to screen for compounds having a desired biological activity.

Accordingly, a general synthetic method is desired that affords optionally substituted lactams in high yield, using economical conditions and reagents, comprising synthetic steps that cleanly provide product having the correct stereochemistry.

In addition, synthetic methods are also desired that economically provide libraries of chemically distinct lactams or compounds derived by further synthesis from lactams, for use, for example, in screening to identify biologically active lead compounds.

SUMMARY OF THE INVENTION

It is therefore a feature and advantage of the present invention, for example, to provide de novo methodology for the synthesis of the lactam core embedded in lactacystin and to refine this technology for general use. As depicted, for example, below, the C—H insertion reaction of diazo compound 4 can lead to the formation of a γ-lactam, which is functionalized at every center. By varying substituents and structures, this method is expanded to formulate a large library of biologically significant lactams and compounds derived therefrom by further synthesis.

Scheme B

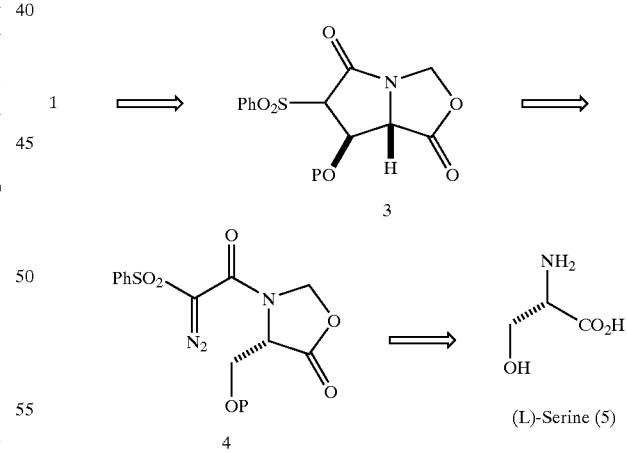

It is another feature and advantage of the present invention to provide the synthetic plan described retrosynthetically in Scheme B. Lactacystin is prepared from bicyclic lactam 3 through sequential alkylation and aldol condensation, and pyrrolidinone 3 is synthesized by employing the aforementioned method. Several representative syntheses will be elaborated upon in this disclosure.

It is a further objective of the present invention to utilize expeditious synthesis of highly substituted γ-lactams and other lactams in an asymmetric manner. These cyclization products are for the total synthesis of numerous natural products and new compounds.

In accordance with yet another embodiment of the present invention, there is provided a compound synthesized from a lactam synthesized by the method of the present invention. Thus, a variety of natural and other compounds are provided that are synthesized using a lactam produced by the method of the present invention. Exemplary compounds, for which facile synthetic routes can be devised starting from suitable lactams produced according to the present invention, include, but are not limited to lactacystin, pramanicin, kainic acid, statine, AHPPA, rolipram, and salts and enantiomers thereof.

There has thus been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended hereto.

In this respect, before explaining at least one embodiment of the invention in detail, it is to be understood that the invention is not limited in its application to the details of the method and to the arrangements of the components set forth in the following description or illustrated in the drawings. The invention is capable of other embodiments and of being practiced and carried out in various ways, Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
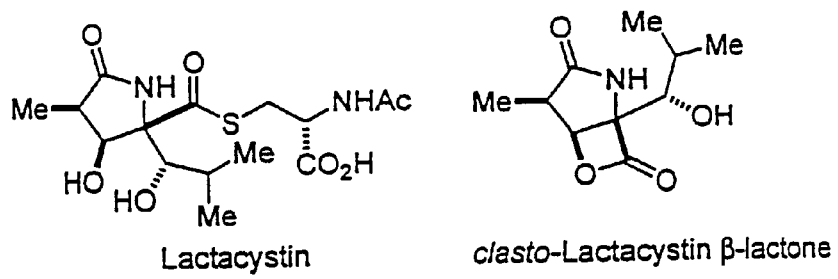
FIG. 1 Illustrates exemplary medicinal pyrrolidinone compounds that are prepared utilizing the lactams and methods of the present invention.
Figure 1:
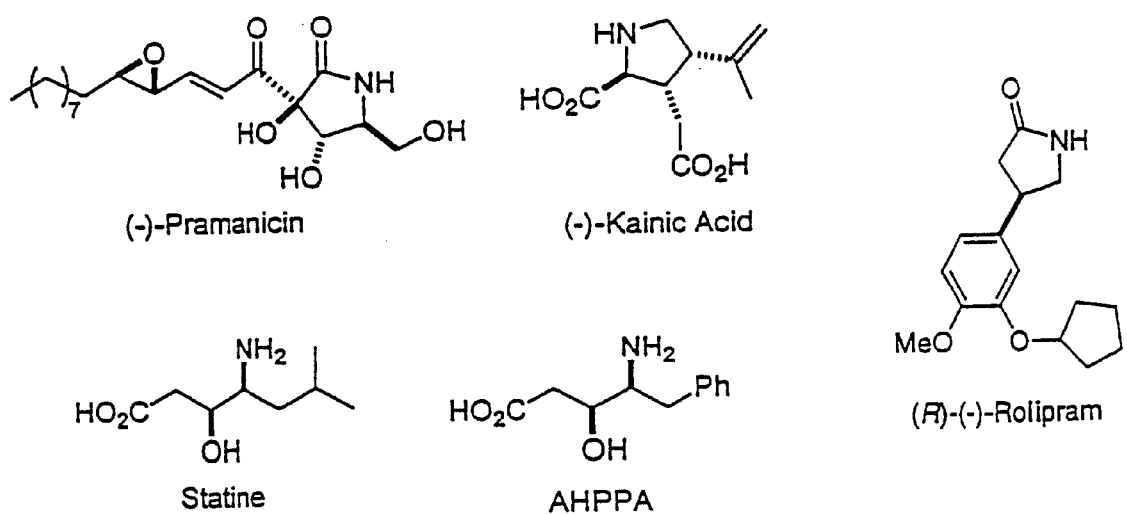

The present invention provides a method of synthesizing a lactam, including γ-lactams, by a method in which an α-diazoacetamide is reacted under conditions promoting intramolecular C—H insertion.

The term α-diazoacetamide as used herein includes compounds of structure (I):

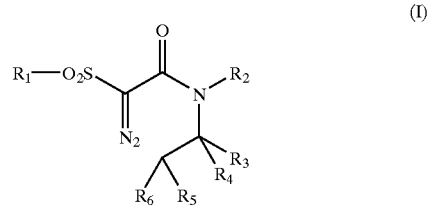

(I)

Where $R_1$, R4, $R_5$, and R6 are, for example, independently H, halo, $N_3$, CN, NC, $(C_1-C_{22})$alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$aralkyl, $(C_7-C_{32})$alkylaryl, $(C_9-C_{32})$aralkenyl, $(C_9-C_{32})$alkenylaryl, OR, SR, $N(R)_2$, NH(R), $CO_2R$, C(O)R, $P(O)(OR)_2$, COR, $CF_3$, S(O)R, or $SO_2R$, wherein each R is independently H, $(C_1-C_{22})$alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$aralkyl, $(C_7-C_{32})$alkylaryl, $(C_9-C_{32})$aralkenyl, or $(C_9-C_{32})$alkenylaryl, where these substituents have the meaning attributed to them herein below.

In preferred embodiments, $R_1$ is phenyl.

In certain embodiments, such as those directed to the synthesis of compounds comprising a pyrrolidinone functionality, $R_2$ and $R_3$ form a ring structure in which R2 and R3 together comprise $(C_1-C_{22})$alkyl, $(C_2-C_{22})$alkenyl, $(C_7-C_{32})$alkylaryl, $(C_9-C_{32})$alkenylaryl, —CH(OH)—CH(CH$_3$)—C(O)—, —C(CH$_3$)$_2$—O—CH$_2$—, —(CH$_2$)$_n$—O—C(O)—, or —C(X)—CH$_2$—O—, where n=0–10, and X is $(C_6-C_{10})$aryl or $(C_7-C_{32})$alkylaryl.

Embodiments directed to the synthesis of compounds comprising a pyrrolidinone functionality include lactam compounds synthesized according to the present invention, which are herein termed "pyrrolidinone precursor" compounds. Such compounds are lactams that have utility in further synthesis using techniques known to those of skill in the art to produce pyrrolidinone containing compounds. Examples of such pyrrolidinones, from which lactam "pyrrolidinone precursor" compounds can be derived by retrosynthesis, include, but are not limited to lactacystin, pramanicin, kainic acid, statine, AHPPA, rolipram, or a salts or enantiomers of these compounds.

In certain other embodiments, such as those directed to the synthesis of compounds comprising a monocyclic lactam, $R_2$ and $R_3$ do not form a ring structure and $R_2$ and $R_3$ are independently H, halo, $N_3$, CN, NC, $(C_1-C_{22})$alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$aralkyl, $(C_7-C_{32})$alkylaryl, $(C_9-C_{32})$aralkenyl, $(C_9-C_{32})$alkenylaryl, OR, SR, $N(R)_2$, NH(R), $CO_2R$, C(O)R, $P(O)(OR)_2$, COR, $CF_3$, S(O)R, or $SO_2R$, wherein each R is independently H, $(C_1-C_{22})$alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$aralkyl, $(C_7-C_{32})$alkylaryl, $(C_9-C_{32})$aralkenyl, or $(C_9-C_{32})$alkenylaryl.

In still other embodiments, wherein $R_1$ is independently $(C_1-C_{22})$alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$arylalkyl, $(C_7-C_{32})$alkylaryl, $(C_9-C_{32})$arylalkenyl, OR, N(R)2, NHR, or $CF_3$;

wherein $R_2$ and $R_3$ are independently one of $(C_1-C_{22})$alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$aralkyl, $(C_7-C_{32})$alkylaryl, $(C_9-C_{32})$arylalkenyl, where the ring portion of any of said aryl, aralkyl, or alkaryl can be optionally substituted; or $R^2$ and $R^3$ when taken together with the nitrogen atom, form a 5- to 7-membered heterocyclic ring, which can be optionally substituted, and which optionally include an additional oxygen, nitrogen or sulfur atom;

wherein $R_{3-6}$ are independently H, halo, N3, CN, NC, $(C_1-C_{22})$alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$arylalkyl, $(C_7-C_{32})$alkylaryl, $(C_9-C_{32})$arylalkenyl, OR, SR, $NR_2$, NH(R), $CO_2R$, C(O)R, $P(O)(OR)_2$, COR, $CF_3$, S(O)R, or $SO_2R$;

$R^3$ and $R^4$ when connected to each other, form 4- to 7-membered carbocyclic ring or heterocyclic ring, which can be optionally substituted, and which optionally include an additional oxygen, or nitrogen atom;

$R^4$ and $R^5$ when connected to each other, form 4- to 7-membered carbocyclic ring or heterocyclic ring, which can be optionally substituted, and which optionally include an additional oxygen, or nitrogen atom; or $R^5$ and $R^6$ when connected to each other, form 4- to 7-membered carbocyclic ring or heterocyclic ring, which can be optionally substituted, and which optionally include an additional oxygen, or nitrogen atom.

The simplified lactam synthesis of the present invention is further directed to production of libraries of lactam compounds, which, for example, can be screened by a suitable assay for a desired biological activity, or can be subjected to further chemical synthetic steps to generate a library of, for example, analogues of pyrrolidinones such as lactacystin, pramanicin, kainic acid, statine, AHPPA, or rolipram.

In promoting intramolecular C—H insertion reactions, which are amply illustrated by the examples herein, certain embodiments comprise the addition of an effective amount of a rhodium salt. In preferred embodiments rhodium tetraacetate, $Rh_2(OAc)_4$, is used to promote intramolecular C—H insertion reactions.

The following definitions are used, unless otherwise described. "Halo" is fluoro, chloro, bromo, or iodo. "Alkyl," "alkoxy," etc. denote both straight and branched groups; but reference to an individual radical such as "propyl" embraces only the straight chain radical, a branched chain isomer such as "isopropyl" being specifically referred to. "Aryl" denotes a phenyl radical or an ortho-fused bicyclic carbocyclic radical having about nine to ten ring atoms in which at least one ring is aromatic. "Cycloalkyl" comprises hydrocarbon ring compounds having between about 3 and 8 ring carbons that are non-aromatic. "Alkenyl" comprises non-cyclic carbon chains having at least one unsaturated bond. "Cycloalkenyl" comprises cyclic carbon chains having between about 5 and 8 carbon atoms and having at least one unsaturated bond. "Aralkyl" comprises an aryl radical attached to an alkyl radical, whereby the combined radicals have between about 7 and 32 carbons and the aryl portion is attached at the position indicated. "Alkylaryl" comprises an alkyl radical attached to an aryl radical, whereby the combined radicals have between about 7 and 32 carbons and the alkyl portion is attached at the position indicated. "Aralkenyl" comprises an aryl radical attached to an alkenyl radical, whereby the combined radicals have between about 9 and 32 carbons and the aryl portion is attached at the position indicated. "Alkenylaryl" comprises an alkenyl radical attached to an aryl radical, whereby the combined radicals have between about 9 and 32 carbons and the alkenyl portion is attached at the position indicated.

It will be appreciated by those skilled in the art that compounds of the invention having one or more chiral center(s) may exist in and be isolated in optically active and/or racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific and preferred values listed below for radicals, substituents, and ranges, are for illustration only; they do not exclude other defined values or other values within defined ranges for the radicals and substituents.

Specifically, "$(C_1-C_{22})$alkyl" can include methyl, ethyl, propyl, isopropyl, butyl, isobutyl, sec-butyl, pentyl, 3-pentyl, hexyl, heptyl, octyl, nonyl, decyl, undecyl, dodecyl, tridecyl, tetradecyl or pentadecyl. "$(C_2-C_{22})$ alkenyl" can include vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl 7-tetradecenyl, 8-tetradecenyl, 9-tetradecenyl, 10-tetradecenyl, 11-tetradecenyl, 12-tetradecenyl, 13-tetradecenyl, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, 14-pentadecenyl.

"$(C_3-C_8)$cycloalkyl" can include cyclopropyl, cyclobutyl, cyclopentyl, cyclohexyl, cycloheptyl, or cyclooctyl.

"$(C_6-C_{10})$Aryl" encompasses substituted and unsubstituted compounds, and can include phenyl, indenyl, 5,6,7,8-tetrahydronaphthyl, or naphthyl. Substituents include, but are not limited to, H, halo, $N_3$, CN, NC, OR, SR, $N(R_2)$, $CO_2R$, $C(O)R$, $P(O)(OR)_2$, $CF_3$, $S(O)R$, and $SO_2R$; wherein each R is independently H, $(C_1-C_{22})$alkyl, $(C_6-C_{10})$aryl, $(C_3-C_8)$cycloalkyl, $(C_2-C_{22})$alkenyl, $(C_5-C_8)$cycloalkenyl, $(C_7-C_{32})$aralkyl, $(C_7-C_{32})$alkylaryl, $(C_9-C_{32})$aralkenyl, and $(C_9-C_{32})$alkenylaryl.

The aforementioned substituents are each optionally substituted with one or more substituents independently selected from the group consisting of halo, nitro, cyano, hydroxy, trifluoromethyl, trifluoromethoxy, $(C_1-C_{15})$alkyl, $(C_2-C_{15})$alkenyl,$(C_2-C_{15})$alkynyl, $(C_3-C_8)$cycloalkyl, $(C_3-C_8)$cycloalkyl$(C_1-C_{15})$alkyl, $(C_3-C_8)$cycloalkyl-$(C_2-C_{15})$alkenyl, $(C_3-C_8)$cycloalkyl$(C_2-C_{15})$alkynyl, $(C_1-C_{15})$alkoxy, $(C_1-C_{15})$alkanoyl, $(C_1-C_{15})$alkanoyloxy, $C(=O)OR$, $C(=O)NR_2$, $OC(=O)OR$, $OC(=O)NR2$.

PHENYLSULFONE α-DIAZOAMIDES

Regarding the chiral pyrrolidinones, natural and unnatural amino acids represent versatile and economical starting materials. However, the amino acids require at some stage of lactam synthesis, a ring closure reaction. Within the scope of the present invention, the intramolecular C—H insertion reaction of certain α-diazoamides, synthesized for example from such amino acids, affords the corresponding γ-lactam.

Studies related to mechanistic pathways involved in intramolecular C—H insertion of diazoamides of the present invention show that ring closure through a C—H insertion is efficient and selective. The present invention therefore not only provides an efficient method, but also offers solutions to the existing problems in carbenoid insertion using amides. A variety of new chiral templates can be created and implemented in numerous asymmetric syntheses, as illustrated herein.

One embodiment of the present invention comprises the use of α-diazoamides with steric and stereoelectronic variations. For example, a sulfonylacetamide is employed to alter electron density as well as steric constraints in such a way, and without being limited thereby by theory, to enhance the reactivity of the incipient rhodium carbenoid and increase regio- and stereoselectivities. As shown in Scheme D, cyclization precursors 9 and 12 are prepared from serine and phenylalanine, respectively, and are subjected to rhodium (ii) mediated C—H insertion catalysis.

2D-NMR techniques. With 12, conversion slow at room temperature, whereas ring closure takes place efficiently under reflux and exhibits similar results to those obtained using serine. It should be noted that the lactams thus produced are fully functionalized, and essentially every center can be further manipulated by appropriate syntheses.

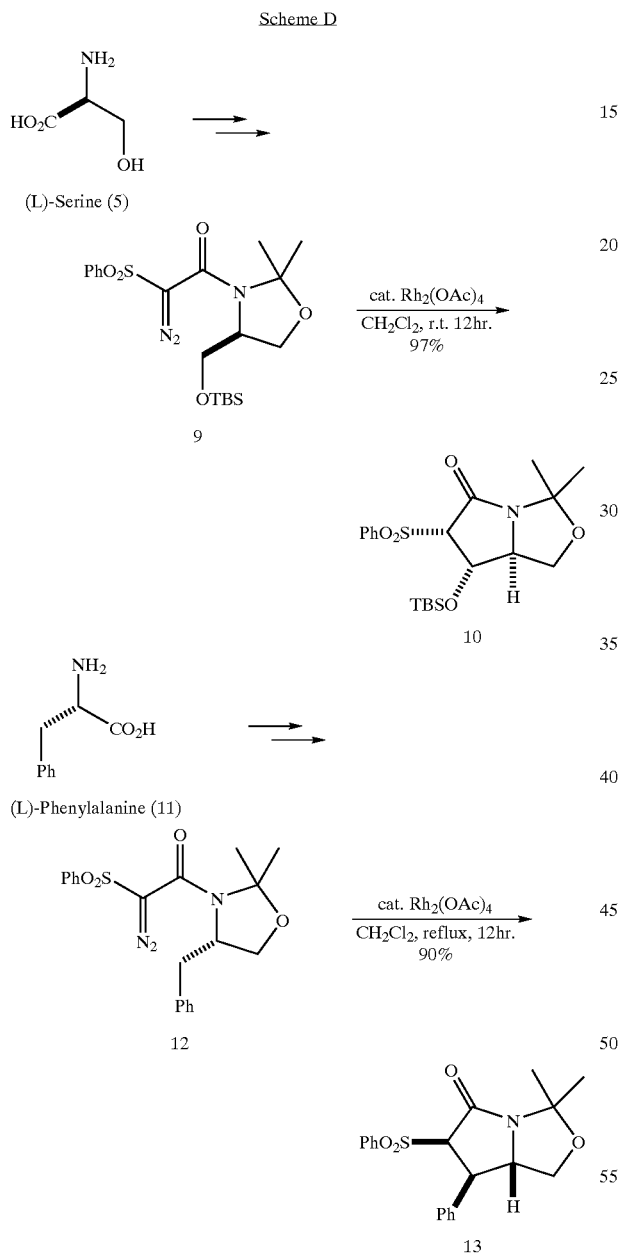

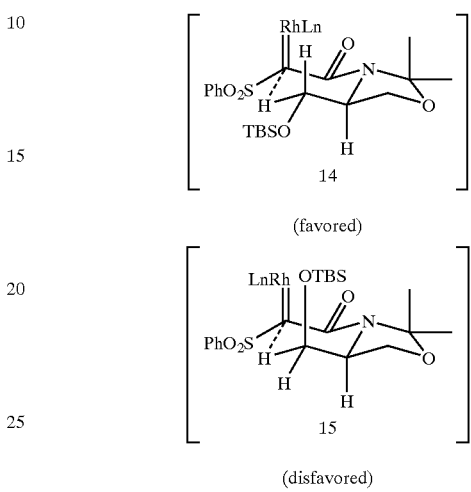

Not to be limited by theory, the observed stereochemical outcomes conform to hypothesized transition states, such as are compared for illustrative purposes only in Scheme E. 1,2-Asymmetric induction, stemming from the amino acid, suggests two possible transition states 14 and 15, wherein the silyl group is located in either the pseudo-equatorial or the pseudo-axial position, respectively. The latter case produced a severe 1,3-diaxial non-bonded interaction, whereas in the former case the molecule adopts a stable chair-like transition state with large groups in the equatorial positions. The phenylsulfone group is rationalized from the observed stereochemistry of products to be in the equatorial position.

These methods are extended to various substrates below to demonstrate the efficacy of the present invention and the high degree of stereoselectivity obtained. Although these examples focus mainly on amino acid-derived substrates for the synthesis of various chiral pyrrolidinones and their derivatives, it should be noted that the methods of the present invention are not confined to the use of amino acid substrates, or to only synthesis of pyrrolidinone-containing lactams.

B. FOUR EXEMPLARY ROUTES FOR SYNTHESIS OF α-DIAZOAMIDES FROM AMINO ACIDS

Prior to the provision of additional specific synthetic examples, four possible embodiments of the present invention are broadly outlined, in the form of four exemplary non-limiting alternative synthetic strategies for lactam synthesis.

Rhodium(II) Catalyzed Intramolecular C—H Insertion of α-Diazoamides Derived From Amino Acids Advantageously, diazo compound 9 is smoothly converted to the desired lactam 10 in 97% yield at room temperature. The reaction proceeds more quickly under reflux of dichloromethane, and neglagable regioisomers are detected. 1,2-Asymmetric induction is specific to give the silyl group in the convex face, while 1,3-induction is greater than 20:1, favoring the syn conformation to the neighboring silyl ether. The stereochemistry is deduced using NOE and

Scheme F

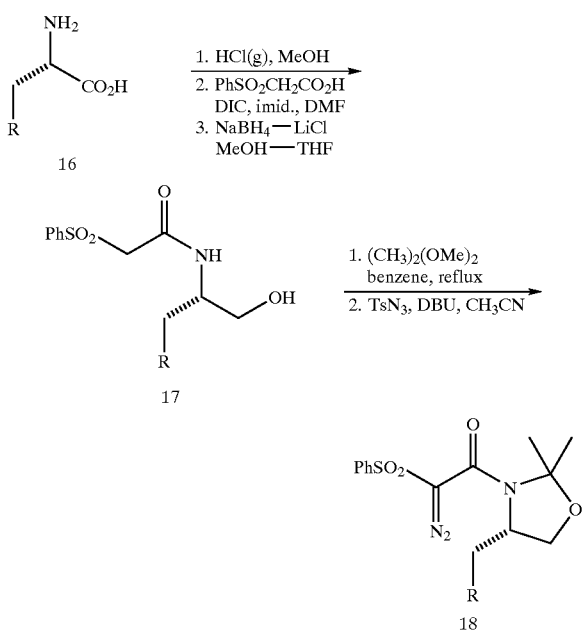

Method A: Utilization of Cyclic Substrates

As delineated in Scheme F, one general synthetic route for α-diazoamides is illustrated. Each amino acid is transformed to sulfonamide 17 by successive esterification, amide formation, and selective ester reduction. After acetonide formation, a diazo transfer gives rise to the cyclization precursors. Diazo transfer is facile and rapid, requiring only approximately 5 minutes.

Scheme G

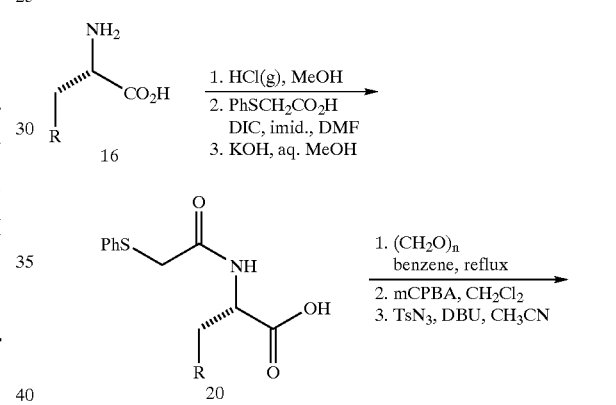

| | | | |
|---|---|---|---|
| (L)-Phenylalanine | R = | —Ph | R' = Silyl |
| (L)-Leucine | | —CH(CH₃)₂ | Allyl |
| (L)-Valine | | —(CH₃)₂ | |
| (L)-Serine | | —OR' | |
| (L)-Threonine | | —(CH₃)OR' | |
| (L)-Cysteine | | —SR' | |
| (L)-Methionine | | —CH₂SMe | |
| (L)-Aspartic acid | | —CO₂R' | |

The diazo compounds are treated with a rhodium catalyst to produce various bicyclic γ-lactams 19, formed via C—H insertion of 18 in a regio- and stereoselective manner. The yields are high, and the ring closure reactions tolerate numerous functionalities, including but not limited to esters and sulfides. Some examples are listed in Scheme G. Difference in reactivities may depend on substituents, which may be exploited in designing the synthesis of structurally complicated natural products.

For example, as demonstrated in Scheme D, the hydrogen adjacent to the silyl ether is prone to insertion, while the hydrogen next to a phenyl group is resistant to insertion at room temperature. In general, and without being limited by theory, hydrogens adjacent to heteroatoms are more reactive than those next to alkyl groups. Electron donating groups facilitate the desired conversions, while a silyl directing effect that promotes C—H insertion adjacent to a silyl ether is observed in the serine case (above).

Method B: Utilization of Cyclic Carbonyl Substrates

Cyclic carbonyl substrates 21 are prepared by using a similar reaction sequence (Scheme H) to the previously discussed method. Masking of carboxylic acids is unavoidable during amide formation, and the ensuing hydrolysis secure amino acids 20.

Scheme H

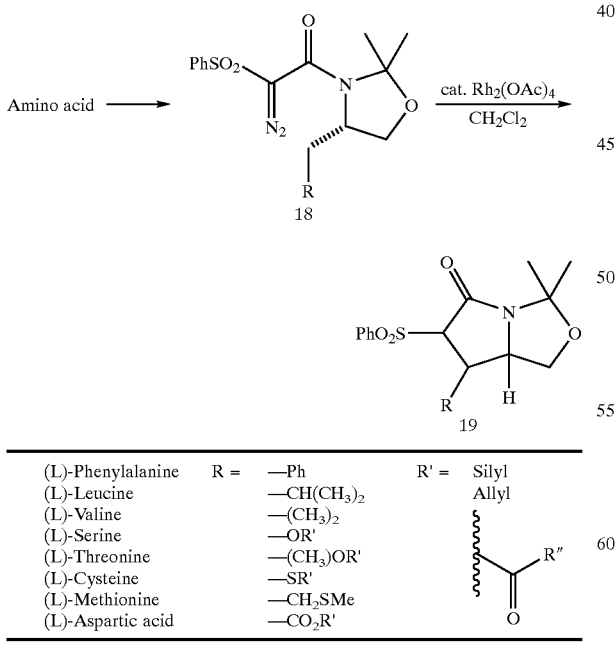

-continued

| | | |
|---|---|---|
| (L)-Phenylalanine | R = —Ph | R' = Silyl |
| (L)-Leucine | —CH(CH₃)₂ | Allyl |
| (L)-Valine | —(CH₃)₂ | |
| (L)-Serine | —OR' | 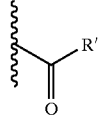 |
| (L)-Threonine | —(CH₃)OR' | |
| (L)-Cysteine | —SR' | |
| (L)-Methionine | —CH₂SMe | |
| (L)-Aspartic acid | —CO₂R' | |

Since the oxidation state of each amino acid is preserved by this method, the produced bicyclic lactam 22 can be more diverse than lactam 19. For example, in a diazo transfer reaction to make 21 with R=benzyl, which stems from phenylalanine, tosyl azide smoothly reacts to provide 21. Method B allows for the production of various cyclic amino esters.

Method C: Utilization of Acyclic Substrates

-continued

| | |
|---|---|
| (L)-Leucine | —CH₂(CH₃)₂ |
| (L)-Valine | —CH(CH₃)₂ |
| (L)-Serine | —OR' |
| (L)-Threonine | —CH(CH₃)OR' |
| (L)-Proline | —(CH₂)₃— |

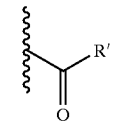

Since acyclic amino esters may undergo side reactions during diazo transfer, it is advantageous to utilize reduced substrates for diazoamide in Scheme I. After the synthesis of amino acid methyl esters, chemoselective mono N-alkylation is carried out (see, Salvatore, R. N., et al., "Cesium Hydroxide Promoted Chemoselective N-Alkylation for the Generally Efficient Synthesis of Secondary Amines" Org. Lett., 1999, vol.1, p. 1893), which is followed by amide formation to give 23. Selective reduction of the ester, silylation and diazo transfer generate acyclic diazo substrates 24.

The C—H insertion reactions undertaken with substrates highlighted in Scheme I, illustrate certain useful aspects. First, regioselectivity and stereoselectivity are excellent, illustrating the generality of the methodology. Five membered lactams are exclusively produced, while the anti selectivities in both 1,2- and 1,3-asymmetric inductions are predominant, possible due to placement of all three substituents in pseudo-equatorial positions.

The first four substrates denoted in Scheme I compare alkyl versus silyl ether groups, among which the silyl group will control the regioselectivity as rationalized above. By employing the substrate 24 derived from serine, the silyl group directing effect is unambiguously demonstrated, which is the first demonstration of a β-silyl effect in C—H insertion of carbenoids.

Method D: Utilization of Cyclic Chiral Auxiliaries

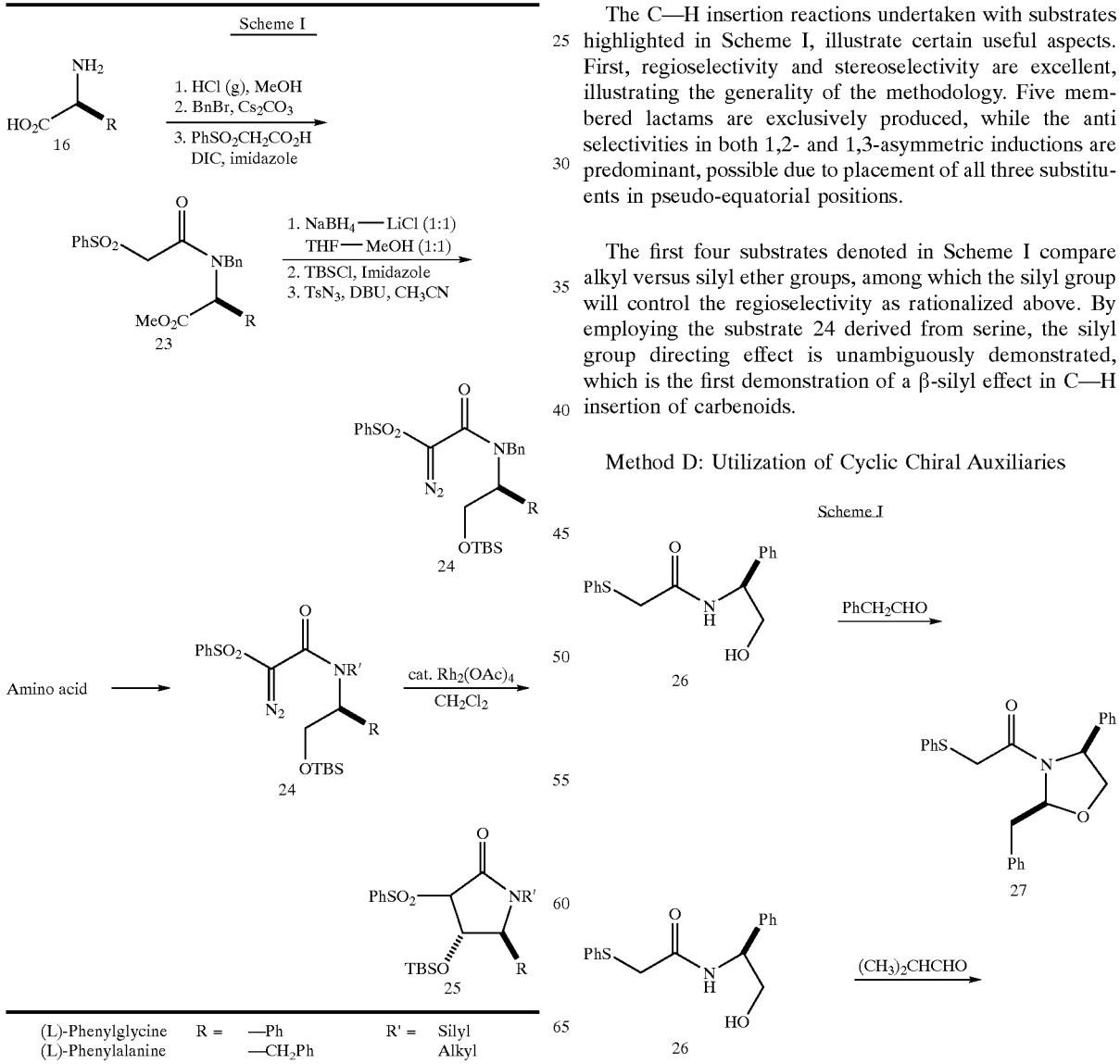

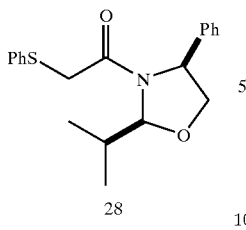

28

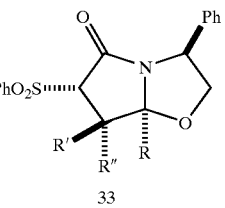

33

R = H, Alkyl, Aromatic, Heterocyclic  
R' = H, Alkyl, Aromatic, Heterocyclic  
R'' = Alkyl, Aromatic, OR''', NR'''$_2$ The present invention comprising C—H insertion technologies applies to non-amino acid substrates. In the present method, amino acid moieties are utilized as chiral auxiliaries as shown in Scheme J. Phenylglycinol is converted to amide 26, which is then subjected to the formation of N,O-acetals where the newly generated stereocenter is governed by the pre-existing asymmetric carbon of phenyl glycine. In turn, this new stereogenicity is transferred to the C—H insertion center, mimicking method A. An advantage of this method is the use of a number of substrates, not only limited to amino acids.

Scheme K

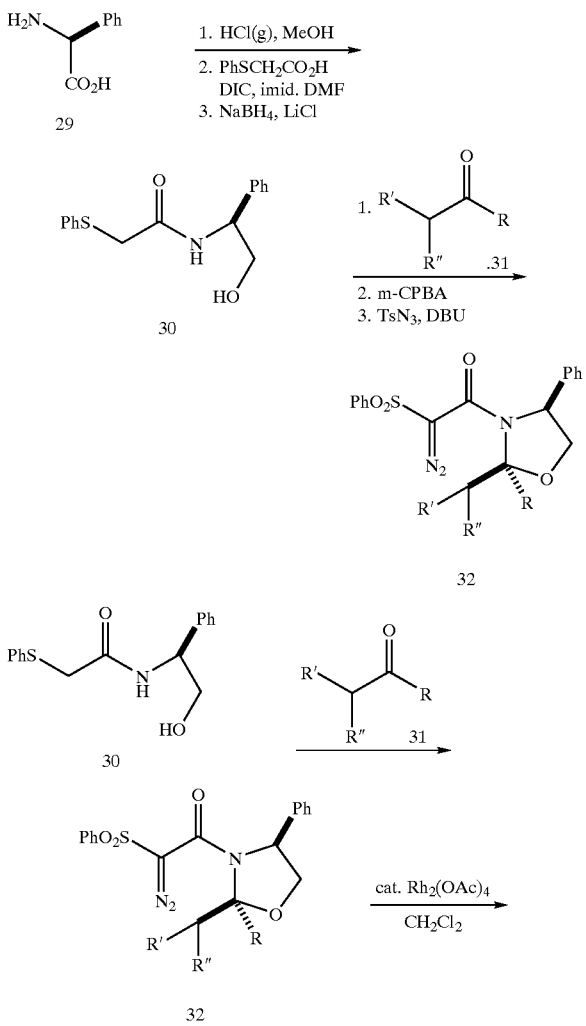

As delineated in Scheme K, phenylglycine 29 is converted to amide 30 using the indicated reactions. Oxidation and diazo transfer are free from any practical problems to provide C—H insertion substrate 32. The cyclic substrate 32 is structurally reminiscent of the cyclization precursor 18 (method A), and similar results are observed.

A variety of carbonyl compounds are employed to produce a library of chiral intermediates for synthesis, which can be utilized in drug screening. Carbonyl substituents are comprised of, for example, alkyl, aromatic, and heterocyclic groups, as well as heteroatoms. In addition to this diversity, asymmetric induction at the unactivated carbon is also envisioned as within the scope of the present invention.

Numerous variations upon the four basic methods broadly outlined above are possible within the scope of the present invention, as will be better understood upon reading the following examples of lactam syntheses, which are provided for illustrative purposes only and are in nowise limiting.

EXAMPLE 1

γ-Lactam Synthesis From Secondary Amines

Total synthesis of γ-lactam from diverse secondary amines is achieved by the present invention according to the following scheme:

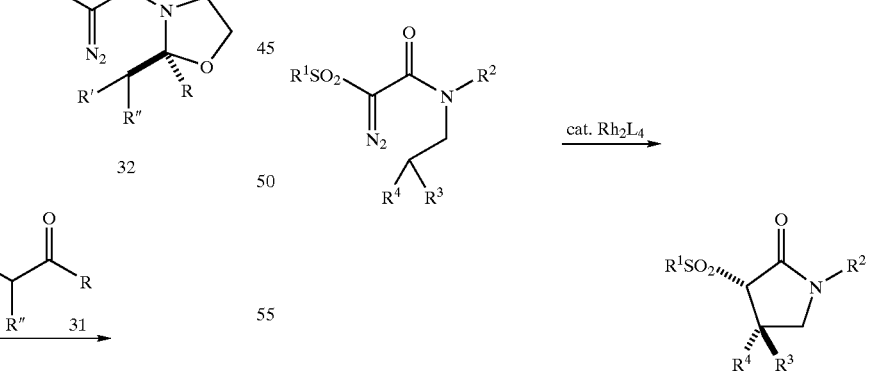

where $R_{1-4}$ include, independently, for example, halo, alkyl, alkoxy, aryl, cycloalkyl, alkenyl, cycloalkenyl, aralkyl, aralkenyl, alkenylaryl. This Example proceeds firstly by a demonstration of two alternative methods for the preparation of α-phenylsulfonylacetamide; secondly by the synthesis of several α-phenylsulfonyl-α-diazoacetamides (a-g); and thirdly by the synthesis of corresponding γ-lactams via C—H insertion.

Preparation of α-Phenylsulfonylacetamide

Method 1

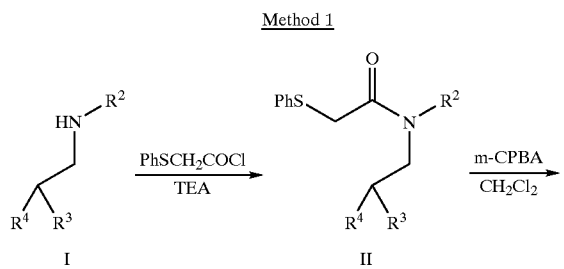

To a mixture of secondary amine I and TEA in anhydrous dichloromethane, are added dropwise a solution of phenylthioacetyl chloride (prepared from phenylthioacetic acid and thionyl chloride) in anhydrous dichloromethane at 0° C. The reaction mixture is warmed to room temperature, stirred for 2 hours, then sat'd NH$_4$Cl solution and dichloromethane are added. The organic layer is washed with brine, dried over Na$_2$SO$_4$, and concentrated to afford α-phenylthioacetamide II, which is used for the next reaction without purification.

To a solution α-phenylthioacetamide II in anhydrous dichloromethane, is added m-CPBA at 0° C. The reaction mixture is stirred for 1 hour at room temperature and then treated with 1 N NaOH solution. The organic layer is washed with brine, dried over Na$_2$SO$_4$, and evaporated. The residue is purified by silica gel column chromatography to give α-phenylsulfonylacetamide III.

Method 2

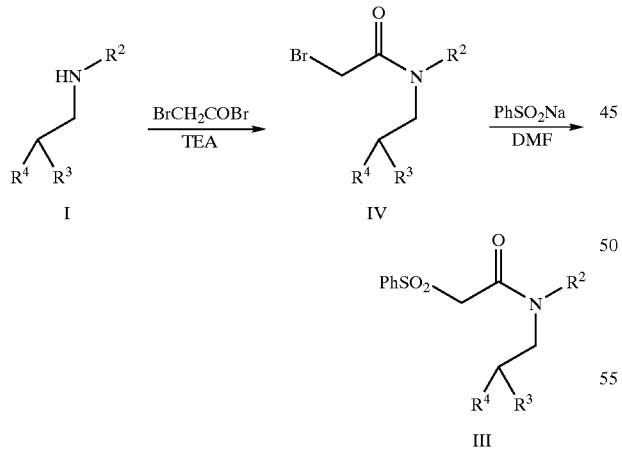

To a mixture of secondary amine I and TEA in anhydrous dichloromethane, is added dropwise a solution of bromoacetyl bromide in anhydrous dichloromethane at 0° C. The reaction mixture is warmed to room temperature, stirred for 2 hours, then sat'd NH$_4$Cl solution and dichloromethane are added. The organic layer is washed with brine, dried over Na$_2$SO$_4$, and concentrated to afford α-bromoacetamide IV, which is used for the next reaction without purification.

To a solution of α-bromoacetamide IV in anhydrous DMF, is added PhSO$_2$Na at 0° C. The reaction mixture is stirred for 1 hour at room temperature and is then poured into water. The organic layer is washed with brine, dried over Na$_2$SO$_4$, and evaporated. The residue is purified by silica gel column chromatography to give α-phenylsulfonylacetamide III.

Preparation of Various α-Phenylsulfonyl-α-diazoacetamides a. α-Phenylsulfonyl-α-diazoacetamide V-1

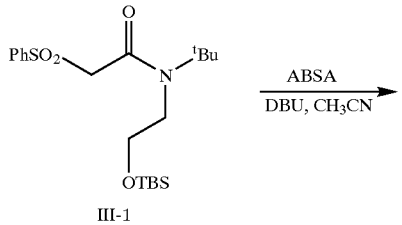

To a solution of the α-phenylsulfonylacetamide 1a and DBU in anhydrous acetonitrile, is added ABSA (p-N-acetylbenzosulfonylazide). The reaction mixture is stirred for 30 min. at room temperature, then poured into water. The aqueous layer is extracted twice with EtOAc. The combined organic layers are washed with 10% aqueous NaOH solution and brine, dried over Na$_2$SO$_4$, and then evaporated. The residue is purified by silica gel column chromatography to give α-diazo-α-phenylsulfonylacetamide as yellow oil.

$^1$H NMR (360 MHz, CDCl$_3$) δ 0.05 (s, 3H), 0.88 (s, 3H), 1.29 (d, 9H), 3.69 (m, 4H), 7.57 (m, 3H), 7.92(m, 2H).

b. α-Phenylsulfonyl-α-diazoacetamide V-2

Following the procedure of the preparation of V-1, α-phenylsulfonyl-α-diazoacetamide V-2 is obtained from α-phenylsulfonylacetamide III-2.

c. α-Phenylsulfonyl-α-diazoacetamide V-3

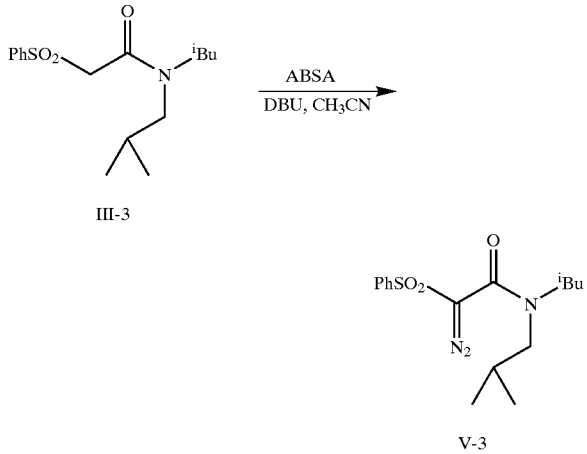

Following the procedure of the preparation of V-1, α-phenylsulfonyl-α-diazoacetamide V-3 is obtained from α-phenylsulfonylacetamide III-3.

d. α-Phenylsulfonyl-α-diazoacetamide V4

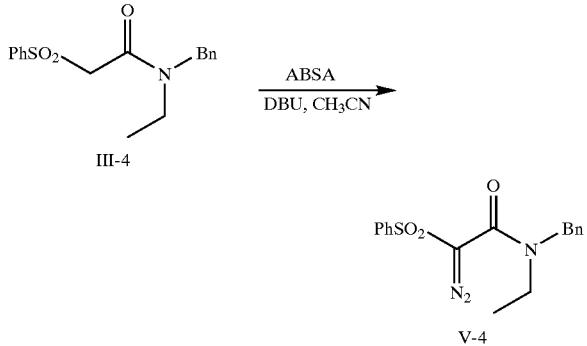

Following the procedure of the preparation of V-1, α-phenylsulfonyl-α-diazoacetamide V4 is obtained from α-phenylsulfonylacetamide III4.

e. α-Phenylsulfonyl-α-diazoacetamide V-5

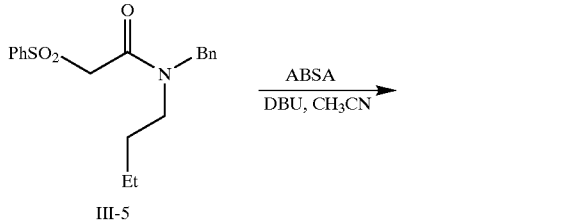

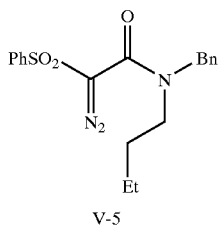

Following the procedure of the preparation of V-1, α-phenylsulfonyl-α-diazoacetamide V-5 is obtained from α-phenylsulfonylacetamide III-5.
$^1$H NMR (360 MHz, CDCl$_3$) δ 0.87(t, 3H, J=7.27 Hz), 1.25 (m, 2H), 1.50 (m, 2H), 3.23 (t, 2H, J=7.67 Hz), 4.56 (s, 2H), 7.24 (m, 5H), 7.60 (m, 3H), 8.02 (m, 2H).

f. α-Phenylsulfonyl-α-diazoacetamide V-6

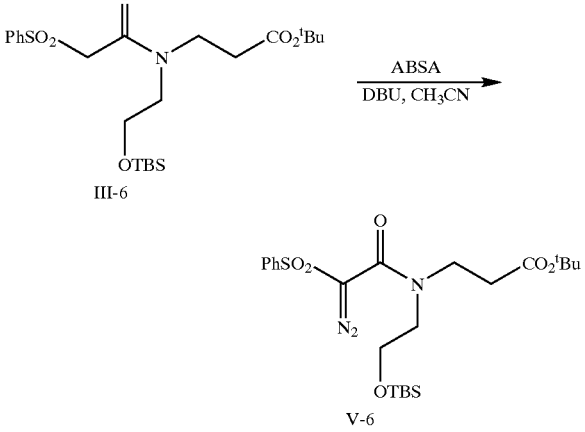

Following the procedure of the preparation of V-1, α-phenylsulfonyl-α-diazoacetamide V-6 is obtained from α-phenylsulfonylacetamide III-6.
$^1$H NMR (250 MHz, CDCl$_3$) δ 0.018 (s, 6H), 0.84 (s, 9H), 1.42 (s, 9H), 2.52 (t, 2H, J=7.14 Hz), 3.49 (t, 2H, J=5.1 Hz), 3.60 (t, 2H, J=7.14 Hz), 3.72 (t, 2H, J=5.1 Hz), 7.59 (m, 3H), 7.99 (d, 2H, J=7.4 Hz)

g. α-Phenylsulfonyl-α-diazoacetamide V-7

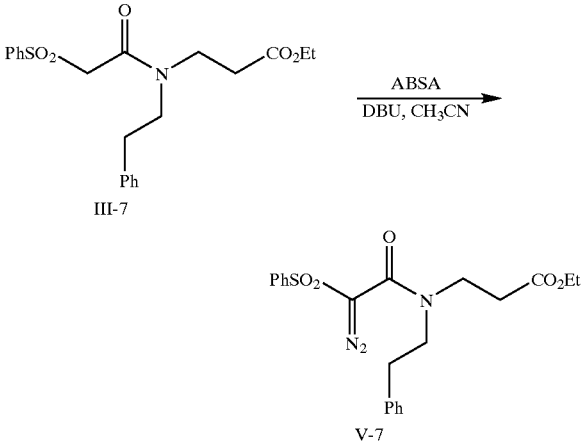

Following the procedure of the preparation of V-1, α-phenylsulfonyl-α-diazoacetamide V-7 is obtained from α-phenylsulfonylacetamide III-7.

The Synthesis of γ-Lactam via C—H Insertion a. γ-Lactam VI-1

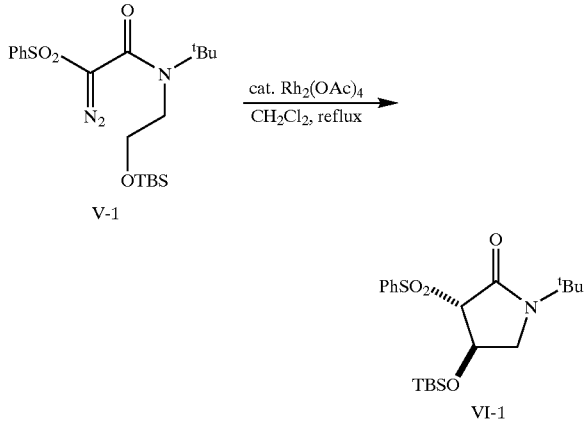

To a solution of α-phenylsulfonyl-α-diazoacetamide V-1 in dry CH$_2$Cl$_2$, is added a catalytic amount of Rh$_2$(OAc)$_4$. The mixture is refluxed with stirring for 12 hours under N$_2$, cooled to room temperature, and is then concentrated. The residue is purified by silica gel column chromatography to give γ-lactam VI-1.

$^1$H NMR (250 MHz, CDCl$_3$) δ 0.11 (d, 6H, J=1.8 Hz), 0.86 (s, 9H), 1.35 (s, 9H), 3.27 (d, 1H, J=10.5 Hz), 3.72 (s, 1H), 3.81 (dd, 1H, J=10.5, 5.3 Hz), 4.87 (d, 1H, J=5.3 Hz), 7.58 (m, 5H).

b. γ-Lactam VI-2

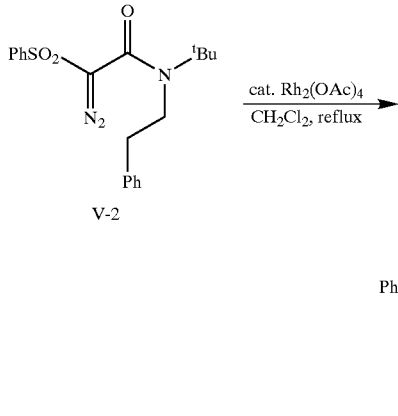

Following the procedure of the preparation of VI-1, γ-lactam VI-2 is obtained from α-phenylsulfonyl-α-diazoacetamide V-2.

$^1$H NMR (250 MHz, CDCl$_3$) δ 1.40 (s, 9H), 3.5 (dd, 1H, J=2.0, 9.7 Hz), 3.88 (d, 1H, J=3.0 Hz), 4.02 (dd, 1H, J=8.0, 9.7 Hz), 4.09 (ddd, 1H, J=2.0, 3.0, 8.0 Hz), 7.25 (m, 5H), 7.58 (m, 3H), 7.93 (d, 2H, J=7.4 Hz).

c. γ-Lactam VI-3

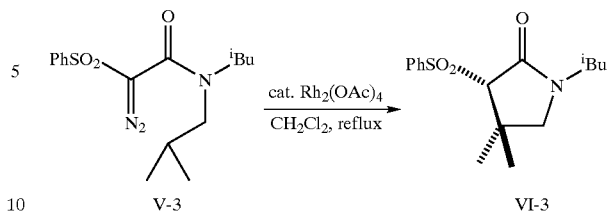

Following the procedure of the preparation of VI-1, γ-lactam VI-3 is obtained from α-phenylsulfonyl-α-diazoacetamide V-3.

$^1$H NMR (250 MHz, CDCl$_3$) δ 0.89 (d, 3H, J=6.6 Hz), 0.95 (d, 3H, J=6.5 Hz), 1.31 (s, 3H), 1.66 (s, 3H)1.89 (m, 1H), 2.95 (m, 2H), 3.22 (dd, 1H, J=8.2, 13.3 Hz), 3.55 (s, 1H), 3.57 (m, 1H), 7.59 (m, 3H), 7.89 (d, 2H, J=7.2 Hz).

d. δ-Lactam VI-4

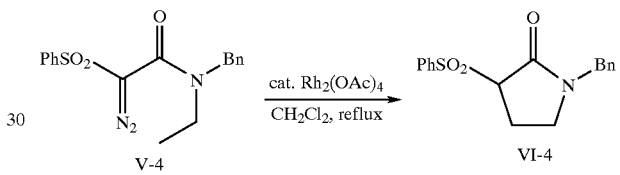

Following the procedure of the preparation of VI-1, γ-lactam VI-3 is obtained from α-phenylsulfonyl-α-diazoacetamide V-3.

$^1$H NMR (360 MHz, CDCl$_3$) 2.44 (m, 1H), 2.73 (m, 1H), 3.20 (m, 1H), 3.36 (m, 1H), 3.94 (dd, 1H, J=4.2, 10.1 Hz), 4.40 and 4.46 (ABq, 2H, 15 Hz), 7.25 (m, 5H), 7.62 (m, 3H), 7.96 (m, 2H).

d. γ-Lactam VI-5

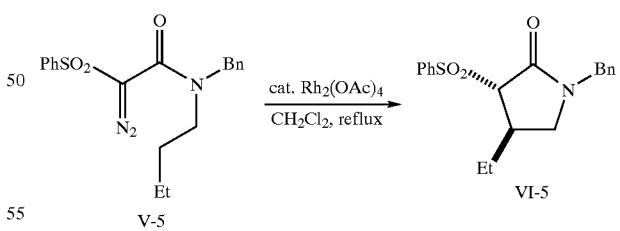

Following the procedure of the preparation of VI-1, γ-lactam VI-5 is obtained from α-phenylsulfonyl-α-diazoacetamide V-5.

$^1$H NMR (360 MHz, CDCl$_3$) δ 0.87 (t, 1H, J=7.3 Hz), 1.48 (m, 1H), 1.62 (m, 1H ), 2.87 (dd, 1H, J=9.1, 3.7 Hz), 3.54 (d, 1H, J=3.7 Hz), 4.41 (dd, 2H, J=28.2, 14.8 Hz), 7.57 (m, 10H); $^{13}$C NMR (90 MHz, CDCl$_3$) δ 10.76, 27.77, 33.92, 46.96, 50.10, 71.30, 127.79, 127.93, 128.75, 128.96, 129.33, 134.13, 135.29, 137.78, 165.06.

e. γ-Lactam VI-6

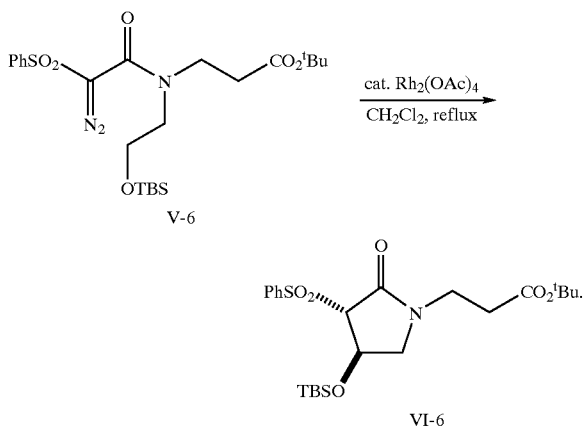

V-6

VI-6

Following the procedure of the preparation of VI-1, α-phenylsulfonylacetamide VI-6 is obtained from α-phenylsulfonylacetamide V-6.

$^1$H NMR (250 MHz, CDCl$_3$) δ 0.12 (s, 3H), 0.13 (s, 3H), 0.87 (s, 9H), 1.44 (s, 9H), 2.47 (t, 2H, J=6.8 Hz), 3.27 (d, 1H, J=10.5 Hz), 3.57 (m, 2H), 3.77 (s, 1H), 3.82 (dd, 1H, J=5.5, 10.5 Hz), 4.99 (d, 1H, J=5.5 Hz), 7.7 (m, 3H), 7.92 (d, 2H, J=7.3 Hz).

f. γ-Lactam VI-7

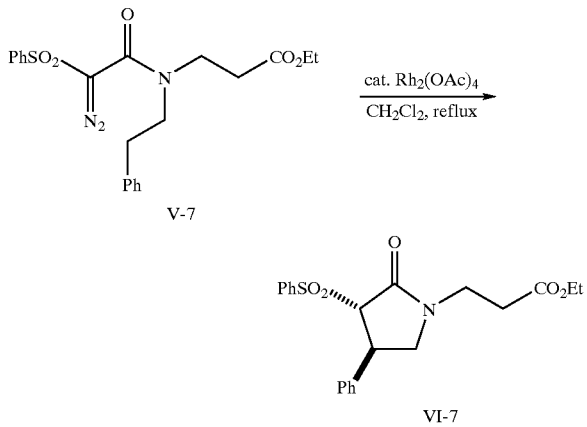

V-7

VI-7

Following the procedure of the preparation of VI-1, α-phenylsulfonylacetamide VI-7 is obtained from α-phenylsulfonylacetamide V-7.

$^1$H NMR (250 MHz, CDCl$_3$) δ 1.25 (t, 3H, J=7.1 Hz), 2.62 (m, 2H), 3.50 (dd, 1H, J=2.5, 10 Hz), 3.66 (dd, 1H, J=5.9, 6.8 Hz), 3.93 (d, 1H, J=3.0 Hz), 4.05 (dd, 1H, J=8.4, 9.89 Hz), 4.14 (q, 2H, J=7.1 Hz), 4.20 (m, 1H), 7.24 (m, 5H), 7.67 (m, 3H), 7.92 (d, 2H, J=7.3 Hz).

The results for Example 1 are collected in Table 2:

TABLE 2

γ-Lactam Synthesis via C—H Insertion reaction

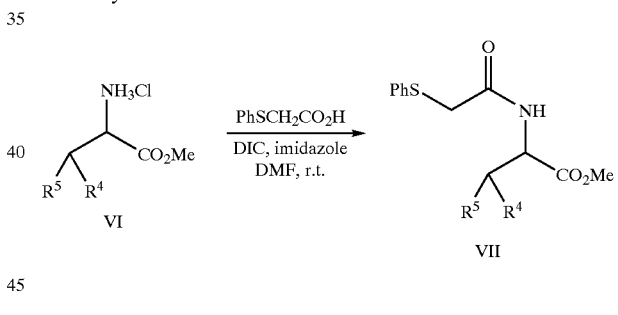

24

| entry | R$^2$ | R$^3$ | R$^4$ | Yield |
|---|---|---|---|---|
| 1 | $^t$Bu | OTBS | H | 93% |
| 2 | $^t$Bu | Ph | H | 88% |
| 3 | $^t$Bu | Me | Me | >99% |
| 4 | Bn | H | H | 60% |
| 5 | Bn | Et | H | 68% |
| 6 | CH$_2$CH$_2$CO$_2$$^t$Bu | OTBS | H | 70% |
| 7 | CH$_2$CH$_2$CO$_2$Et | Ph | H | 78% |

EXAMPLE 2

Preparation of C—H Insertion Reaction Precursors From Amino Acids

α-Phenylthioacetamide

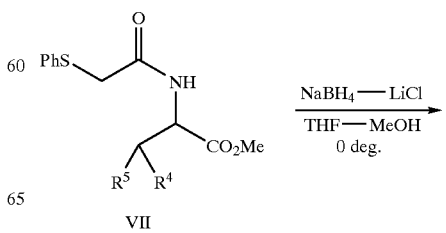

VI → VII

To a solution of amino acid methyl ester VI and imidazole in DMF, is added phenylthioacetic acid followed by diisopropylcarbodiimide at room temperature. The reaction mixture is stirred for 12 hours. After filtration on silica gel pad, the filtrate is poured into water and EtOAc. The organic layer is washed twice with water, dried over Na$_2$SO$_4$, and concentrated to afford α-phenylthioacetamide VII.

Alcohol

VII → (NaBH$_4$—LiCl, THF—MeOH, 0 deg.)

-continued

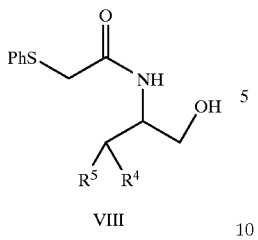

VIII

To a solution of α-phenylthioacetamide VII in methanol and THF (v/v=1/1), is added LiCl followed by NaBH$_4$ at 0° C. The reaction mixture is stirred for 1 hour and concentrated under reduced pressure. The residue is diluted with EtOAc, which is washed with 2 N HCl and brine, dried over Na$_2$SO$_4$, and concentrated to afford VIII.
Ketalization

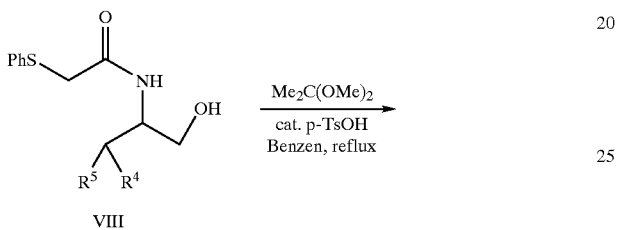

To a solution of alcohol VIII in benzene, is added 2,2-dimethoxypropane and a catalytic amount of p-TsOH. The reaction mixture is refluxed for 1 hour, then slowly distilled. The reaction mixture is partitioned between sat'd NaHCO$_3$ solution and ethyl ether. The organic layer is washed with brine, dried over Na$_2$SO$_4$ and concentrated to give crude product, which is column chromatographed to give IX.
α-Phenylsulfonylacetamide

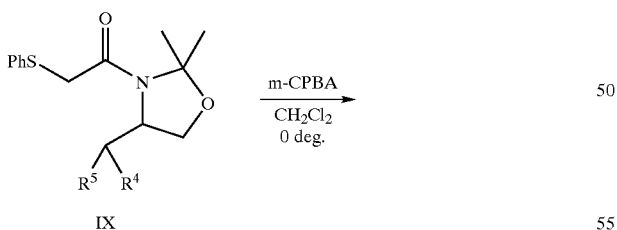

To a solution α-phenylthioacetamide IX in anhydrous dichloromethane, is added m-CPBA at 0° C. The reaction mixture is stirred for 1 hour at room temperature and then treated with 1 N NaOH solution. The organic layer is washed with brine, dried over Na$_2$SO$_4$, and evaporated. The residue is purified by silica gel column chromatography to give α-phenylsulfonylacetamide X.

EXAMPLE 3

α-Phenylsulfonyl-α-Diazoacetamide
a. α-Phenylsulfonyl-α-Diazoacetamide XI-1

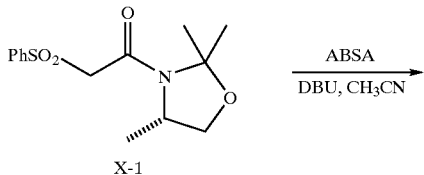

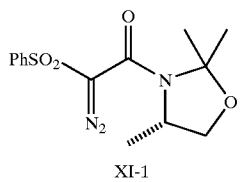

XI-1

To a solution of the α-phenylsulfonylacetamide X-1 and DBU in anhydrous acetonitrile, is added ABSA (p-N-acetylbenzosulfonylazide). The reaction mixture is stirred for 30 min. at room temperature and is then poured into water. The aqueous layer is extracted twice with EtOAc. The combined organic layer is washed with 10% aqueous NaOH solution and brine, dried over Na$_2$SO$_4$, and then evaporated. The residue is purified by silica gel column chromatography to give α-phenylsulfonyl-α-diazoacetamide XI-1 as yellow oil.

$^1$H NMR (360 MHz, CDCl$_3$) δ 1.31 (d, 3H, J=5.7 Hz), 1.40 (s, 3H), 1.60 (s, 3H), 3.67 (dd, 1H, J=3.0, 5.5 Hz), 3.98 (m, 1H), 4.05 (dd, 1H, J=5.5, 6.3), 7.58 (m, 3H), 8.0 (d, 2H, J=7.5 Hz).

b. α-Phenylsulfonyl-α-Diazoacetamide XI-2

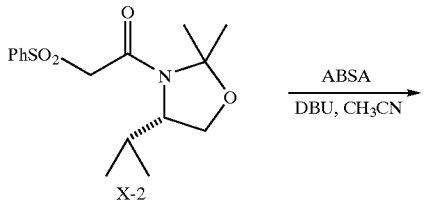

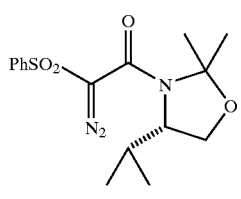

XI-2

Following the procedure of the preparation of XI-1, α-phenylsulfonylacetamide XI-2 is obtained from α-phenylsulfonylacetamide X-2.

$^1$H NMR (250 MHz, CDCl$_3$) δ 0.90 (d, 3H, J=6.7 Hz), 0.95 (d, 3H, J=7.0), 1.40 (s, 3H), 1.64 (s, 3H), 2.1 (m, 1H), 3.81 (m, 1H), 3.93 (m, 2H), 7.61 (m, 3H), 8.0 (d, J=7.1 Hz).

c. α-Phenylsulfonyl-α-Diazoacetamide XI-3

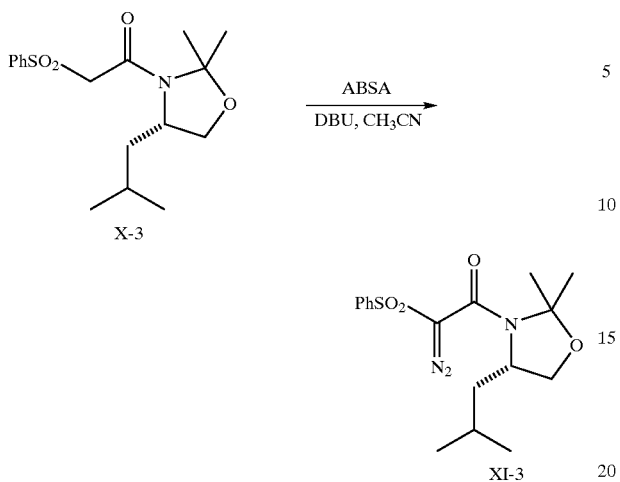

Following the procedure of the preparation of XI-1, α-phenylsulfonylacetamide XI-3 is obtained from α-phenylsulfonylacetamide X-3.

$^1$H NMR (250 MHz, CDCl$_3$) δ 1.35 (s, 3H), 1.69 (s, 3H), 2.82 (dd, 1H, J=9.3, 13.4), 3.08 (dd, 1H, J=5.3, 13.4), 3.85 (d, 2H, J=3.6), 4.3 (m, 1H), 7.26 (m, 5H), 7.57 (m, 3H), 7.94 (d, 2H, J=7.2).

d. α-Phenylsulfonyl-α-Diazoacetamide XI-4

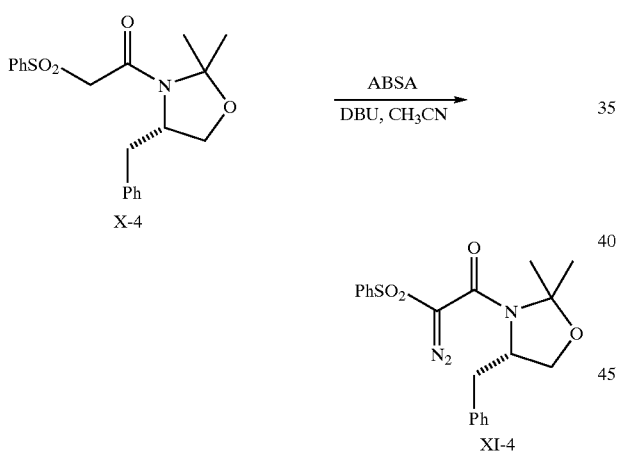

Following the procedure of the preparation of XI-1, α-phenylsulfonylacetamide XI4 is obtained from α-phenylsulfonylacetamide X-4.

$^1$H NMR (360 MHz, CDCl$_3$) δ 0.07 (s, 3H), 0.08 (s, 3H), 0.87 (s, 9H), 1.42(s, 3H), 1.59 (s, 3H), 3.65 (m, 2H), 3.98 (m, 3H), 7.62 (m, 3H), 8.01 (m, 2H).

e. α-Phenylsulfonyl-α-Diazoacetamide XI-5

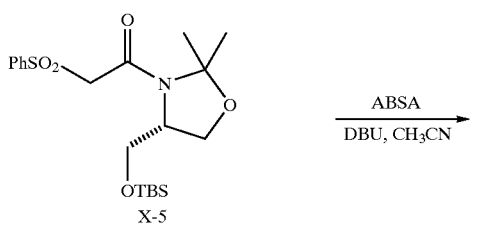

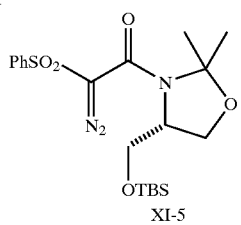

Following the procedure of the preparation of XI-1, α-phenylsulfonylacetamide XI-5 is obtained from α-phenylsulfonylacetamide X-5.

$^1$H NMR (360 MHz, CDCl$_3$) δ 0.07 (s, 3H), 0.08 (s, 3H), 0.87 (s, 9H), 1.42 (s, 3H), 1.59 (s, 3H), 3.65 (m, 2H), 3.98 (m, 3H), 8.01 (m, 2H).

f. α-Phenylsulfonyl-α-Diazoacetamide XI-6

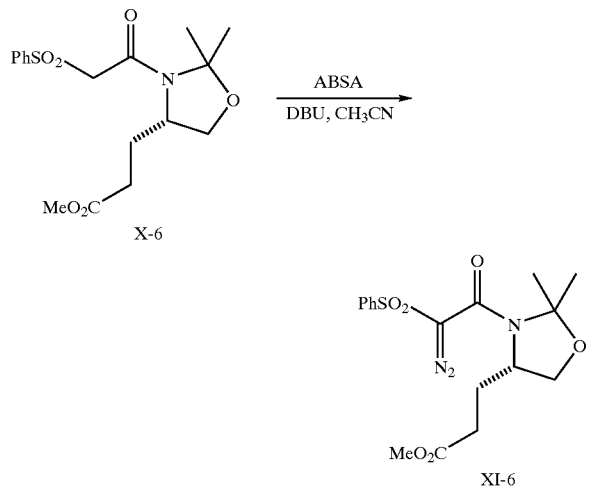

Following the procedure of the preparation of XI-1, α-phenylsulfonylacetamide XI-6 is obtained from aα-phenylsulfonylacetamide X-6.

EXAMPLE 4

The Synthesis of γ-Lactam via C—H Insertion a. γ-Lactam XII-1

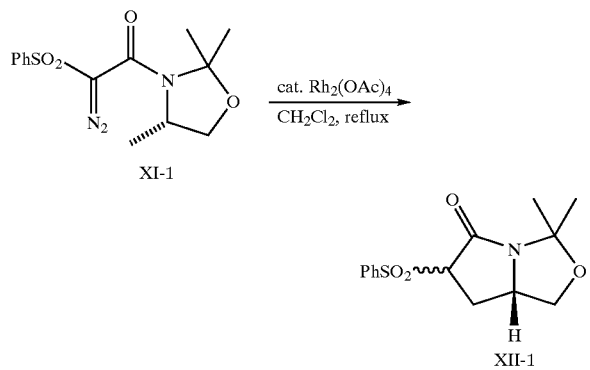

To a solution of the α-phenylsulfonyl-α-diazoacetamide XI-1 in dry CH$_2$Cl$_2$, is added a catalytic amount of Rh$_2$(OAc)$_4$. The mixture was refluxed with stirring for 12 hours under N$_2$, cooled to room temperature, and is then concentrated. The residue is purified by silica gel column chromatography to give γ-lactam XII-1.

¹H NMR (250 MHz, CDCl₃) δ 1.39 (s, 3H), 1.57 (s, 3H), 2.24 (m, 1H), 2.92 (m, 1H), 3.41 (m, 1 HZ, 4.27 (m, 1H), 4.32 (m, 1H), 4.41 (m, 1H), 7.62 (m, 3H), 7.91 (m, 2H).

b. γ-Lactam XII-2

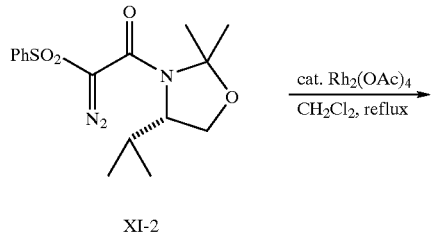

Following the procedure of the preparation of XII-1, α-phenylsulfonylacetamide XII-2 is obtained from α-phenylsulfonylacetamide XI-2.

¹H NMR (360 MHz, CDCl₃) δ 1.16 (s, 3H), 1.37 (s, 3H), 1.55 (s, 3H), 1.64 (s, 3H), 7.60 (m, 3H), 7.95 (m, 2H).

c. γ-Lactam XII-3

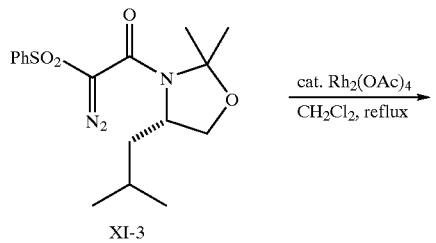

Following the procedure of the preparation of XII-1, α-phenylsulfonylacetamide XII-3 is obtained from α-phenylsulfonylacetamide XI-3.

¹H NMR (250 MHz, CDCl₃) δ 0.95 (d, 3H, J=6.9 Hz), 1.03 (d, 3H, J=6.7 Hz), 1.45 (s, 3H), 1.62 (s, 3H), 2.22 (m, 1H), 2.79 (m, 1H), 3.59 (dd, 1H, J=8.0, 9.3 Hz), 3.89 (ddd, 1H), J=5.5, 5.6, 9.3 Hz), 4.07 (dd, 1H, J=5.5, 8.0 Hz), 4.16 (d, 1H, J=8.2 Hz), 7.68 (m, 3H), 8.0 (d, 2H, J=7.3 Hz).

d. γ-Lactam XII-4

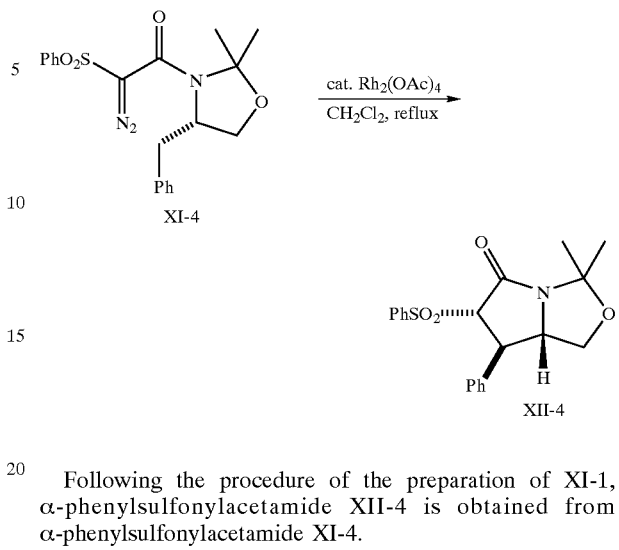

Following the procedure of the preparation of XI-1, α-phenylsulfonylacetamide XII-4 is obtained from α-phenylsulfonylacetamide XI-4.

¹H NMR (250 MHz, CDCl₃) δ 1.45 (s, 3H), 1.65 (s, 3H), 3.68 (dd, 1H, J=7.9, 8.0 Hz), 3.88 (dd, 1H, J=6.2, 9.1 Hz), 4.1 (m, 2H), 4.5 (d, 1H, J=9.1 Hz), 7.3 (m, 5H, Ph), 7.50 7.6 (m, 3H), 7.91 (d, 2H, J=7.2 Hz).

e. γ-Lactam XII-5

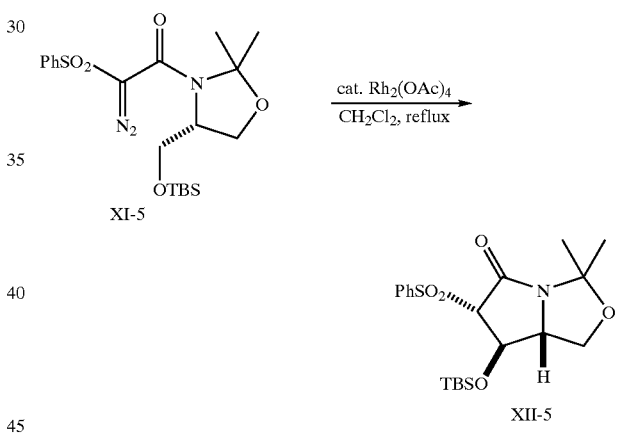

Following the procedure of the preparation of XII-1, α-phenylsulfonylacetamide XII-5 is obtained from α-phenylsulfonylacetamide XI-5.

¹H NMR (360 MHz, CDCl₃) δ 0.15 (s, 3H), 0.24 (s, 3H), 0.93 (s, 9H), 1.47 (s, 3H), 1.59 (s, 3H), 3.59 (dd, 1H, J=10.3, 9.4 Hz), 3.97 (m, 1H), 4.16 (dd, 1H, J=8.2, 6.8 Hz), 4.26 (d, 1H, J=6.8 Hz), 4.83 (dd, 1H, J=6.8, 4.9 Hz), 7.62 (m, 3H), 7.9 (d, 2H, J=7.2 Hz).

f. γ-Lactam XII-6

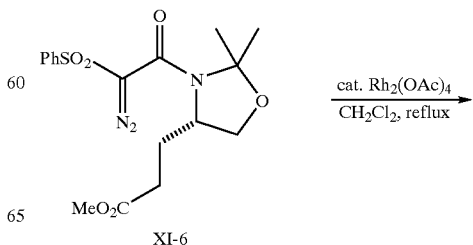

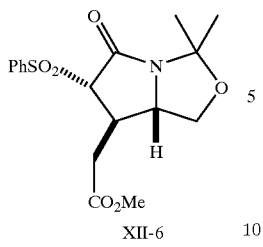

XII-6

Following the procedure of the preparation of XII-1, α-phenylsulfonylacetamide XII-6 is obtained from α-phenylsulfonylacetamide XI-6.

¹H NMR (250 MHz, CDCl₃) δ 1.43 (s, 3H), 1.52 (s, 3H), 2.71 (dd, 1H, J=15.5, 10.5 Hz), 3.13 (m, 1H), 3.27 (dd, 1H, J=15.5 3.3 Hz), 3.61 (t, 1H, J=8.9 Hz), 3.76 (s, 3H), 3.85 (m, 1H), 4.25 (m, 2H), 7.55 (m, 5H).

The results for this Example are collected in Table 3:

TABLE 3

Stereoselective γ-Lactam Synthesis from Amino Acid

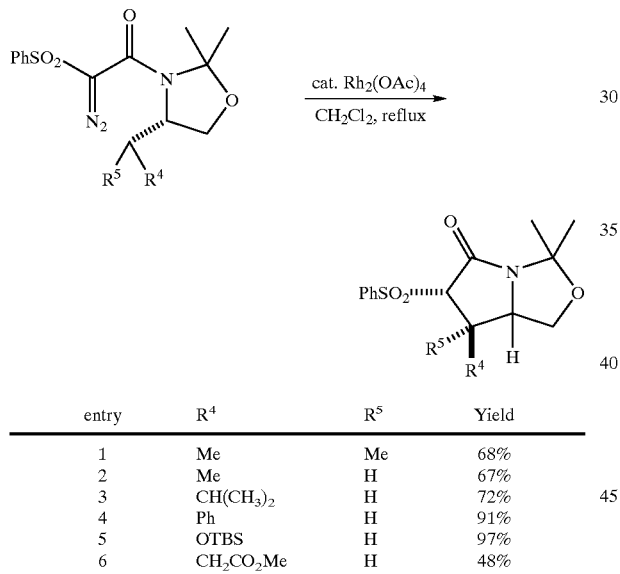

| entry | R⁴ | R⁵ | Yield |
|---|---|---|---|
| 1 | Me | Me | 68% |
| 2 | Me | H | 67% |
| 3 | CH(CH₃)₂ | H | 72% |
| 4 | Ph | H | 91% |
| 5 | OTBS | H | 97% |
| 6 | CH₂CO₂Me | H | 48% |

EXAMPLE 8

Total Synthesis of Lactacystin

Central to the synthesis of lactacystin and its analoges is the stereoselectivity of the key step, namely intramolecular C—H insertion, which is further demonstrated herein. Hence, a α-diazoamide containing serine moiety is prepared in an expeditious fashion as delineated below. As discussed earlier, the reaction is efficient and the observed stereoselectivity is good. Because the cyclization product is only a few simple steps from the natural product, the total synthesis of lactacystin is completed, and the newly formed stereochemistry is confirmed through spectral comparison with the natural product.

Scheme L

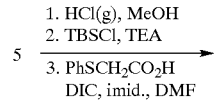
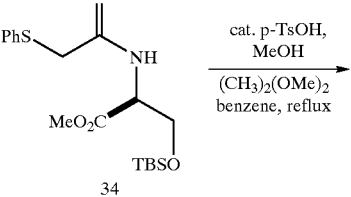

34

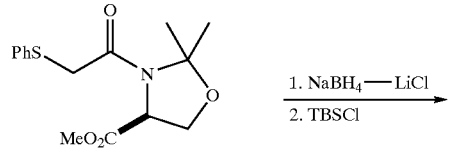

35

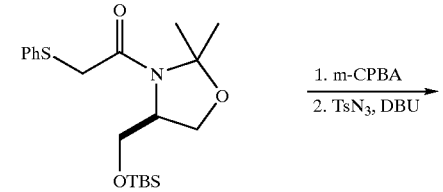

36

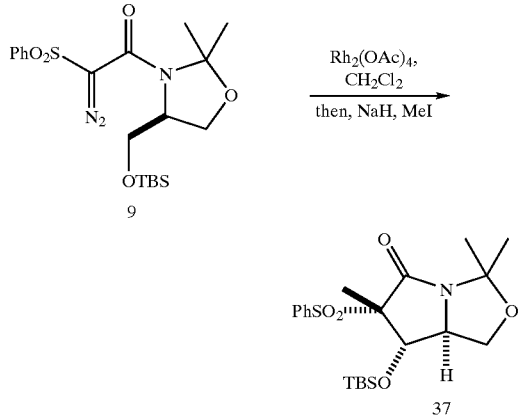

Starting with (L)-serine, β-phenylsulfonylamide 34 is made almost quantitatively by esterification, silylation, and amidation. Removal of the silyl protecting group gives the primary alcohol, which is assembled with the amide as an acetonide. Ester 35 is subjected to selective reduction and the resulting alcohol is masked as TBS ether. Sequential oxidation and diazo transfer provide the cyclization precursor in high yield. Intramolecular C—H insertion yields the pyrrolidinone ring and the ensuing methylation generates a single diastereomer 37. As expected, the methyl group is introduced away from the bulky. neighboring group. With the exception of the silylation and acetonide formation, each step gives high yields (>90%) without side product formation, and bicyclic lactam 37 is obtained on a multigram scale.

Expeditious Synthesis of Lactacystin

Methylated lactam 37 has the unnatural stereochemistry at the silyl ether bearing carbon, and the synthesis of the unnatural enantiomer is performed, for unambiguous elucidation of relative stereochemistry. After RuO₄ oxidation, an aldol condensation forms the C—C bond at the ring junction, and the stereochemistry is controlled by the pre-existing ether group. Aldol stereochemistry also favors the desired configuration. Desulfonylation and removal of the acetonide secures the dihydroxyacid 39, which is a common intermediate for the synthesis of lactacystin. As this compound is two steps away from the target, the overall synthesis in the unnatural form requires 17 steps, and the yield of each step is satisfactory. One notable feature in this synthesis is to utilize the stereochemistry of an amino acid for stereochemical sense at the adjacent ether center, which in turn controls the stereochemistry at the other two carbons. Stereocontrol is highly feasible due to the rigidity of the bicyclic lactam, which is a crucial feature in asymmetric synthesis.

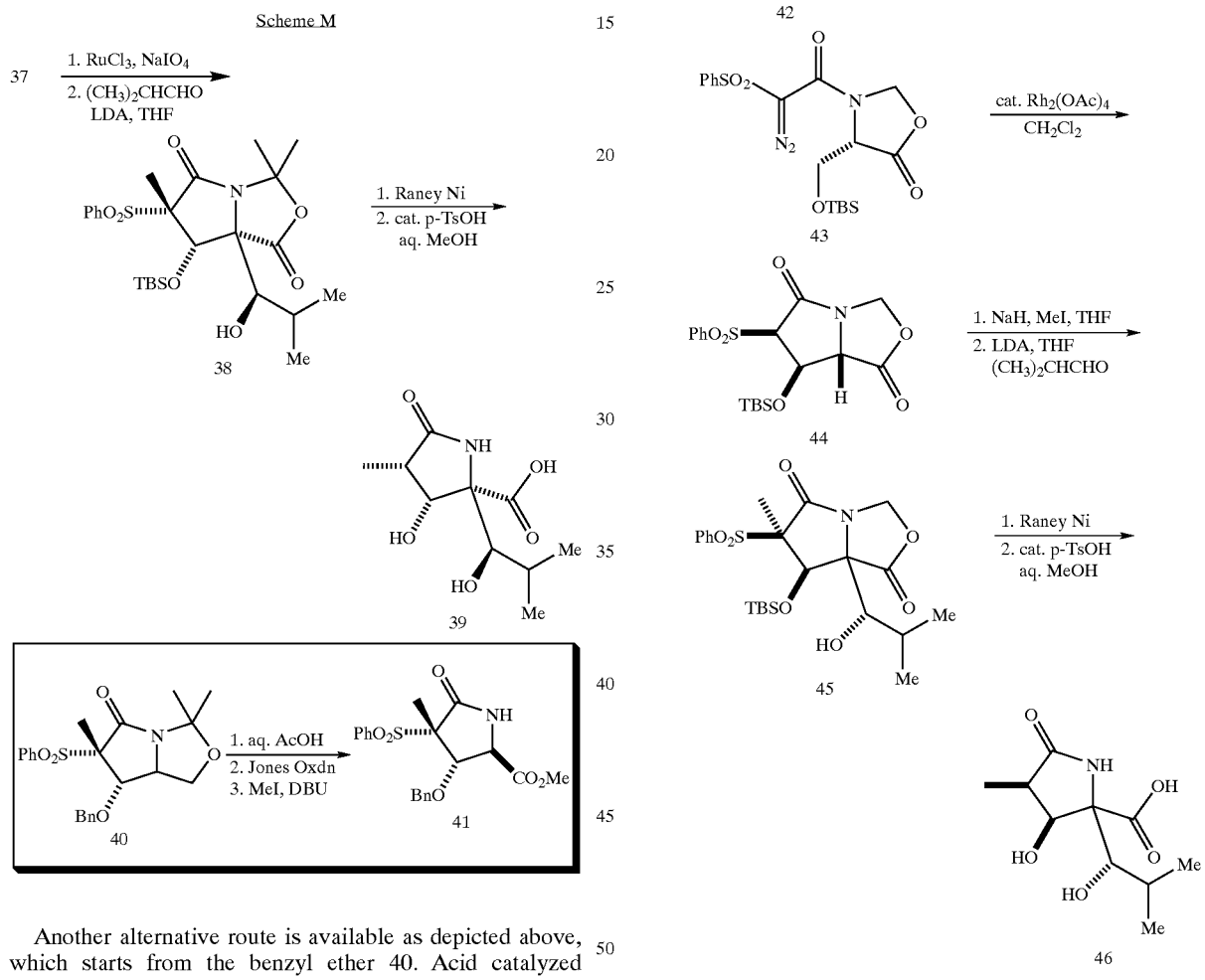

Another alternative route is available as depicted above, which starts from the benzyl ether 40. Acid catalyzed hydrolysis followed by Jones oxidation affords the corresponding carboxylic acid, which is methylated to furnish ester 41. Using similar sequences, this monocyclic intermediate is transformed to the known compound for the natural product synthesis.

Subsequently, synthesis of the natural form is initiated, as described herein. The aforementioned synthesis adopts method A, while the present route exploits route B. Synthesis begins with the protection of each serine functionality to provide β-sulfonylamide 42, which are converted to diazo compound 43 following the previously schemes. Cyclization, via a C—H insertion reaction, produces bicyclic lactam 44. Methylation and aldol condensation secure the necessary functional groups and deprotection of masking groups secures the natural stereochemistry. To reach this intermediate requires eleven steps.

Synthesis of acyclic substrates for γ-lactam synthesis (method C) in pursuit of clasto-lactacystin β-lactone (2), is summarized herein. The cesium base promoted alkylation of serine gives rise to predominant formation of N-benzylserine benzyl ester without affecting hydroxyl, and this product forms the β-lactone under various basic conditions to give lactone 48 after the introduction of β-phenylsulfonylacetic acid. Since the [3.2.0] bicycloheptane system is being prepared, the 1,2-asymmetric induction are exclusively favored to cis fused ring 50.

Methylation and aldol condensation is smooth and stereoselective, and removal of sulfonyl and benzyl groups delivers lactone 2. The synthesis consists of eight steps.

In addition, the targeted natural products can also be synthesized by method C (acyclic substrates).

Scheme O

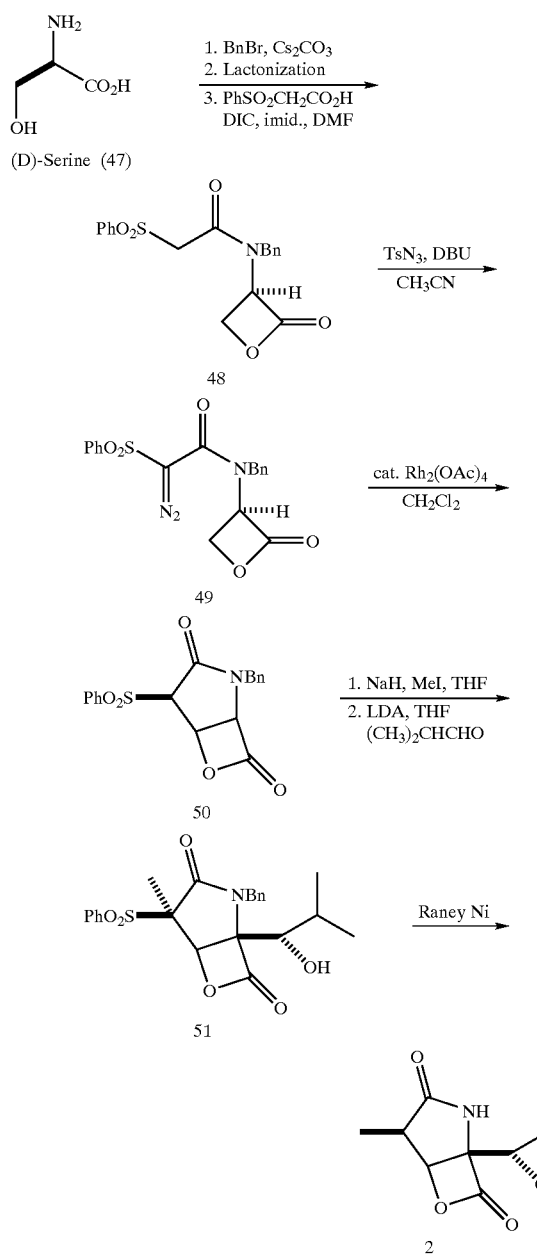

In the disclosed syntheses, the feasibility of these three methods is demonstrated in γ-lactam synthesis via an intramolecular rhodium(II) catalyzed C—H insertion of α-diazo-β-phenylsulfonylacetamides containing amino acid derivatives. These syntheses also illustrate features in asymmetric synthesis, which are 1,2- and 1,3-asymmetric induction during C—C bond formations.

In the above lactacystin syntheses, three different methods of C—H insertion are utilized. The following section further illustrates use of the γ-lactam synthons in several natural product syntheses via all four aforementioned methods.

EXAMPLE 9

Synthesis of Pramanicin by Method A

Pramanicin is isolated from a fungus, Stagonospora, and comprises a highly functionalized γ-lactam headgroup (FIG. 1). This compound also exhibits activity against the acapsular form of *Cryptococcus neoformans*.

Scheme P

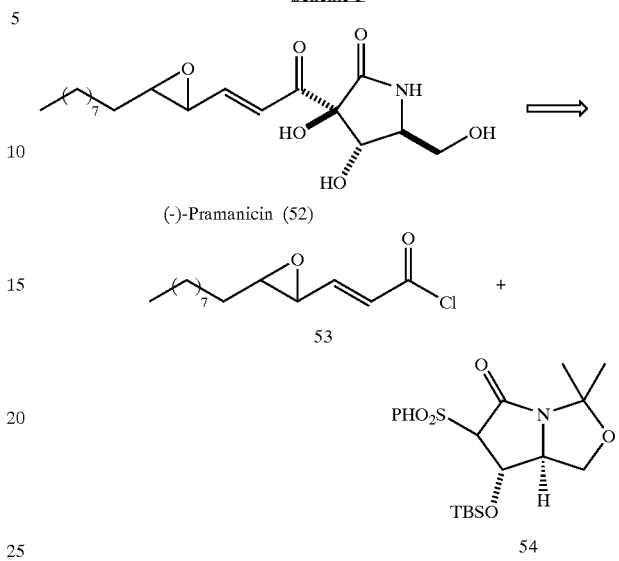

Bicyclic γ-lactam 54, which is derived from (L)-serine via method A. The acid chloride 53 or corresponding aldehyde is introduced to the α-center of γ-lactam 54, and the resulting coupling product is subjected to removal of protecting groups. Hydroxylation at the α-center is carried out by using one of several conventional methods.

EXAMPLE 10

Synthesis of Kainic Acid by Method B

Kainic acid is a neuronal excitant and has facilitated research on Alzeheimer's disease and epilepsy. In this example, a 9 step synthesis is disclosed as shown below. This synthesis is performed using the strategy similar to the previously discussed method B.

Starting with glutamic acid, selective protection of α-amino acid moieties followed by esterification of the residual γ-acid ensures the formation of oxaolidinone 56, which in turn is converted to diazoamide 57 through sequential amide formation and diazo transfer. Applying the C—H insertion protocol (method B), bicyclic lactam 58 is prepared in a stereoselective manner.

Scheme Q

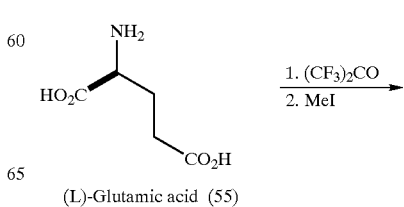

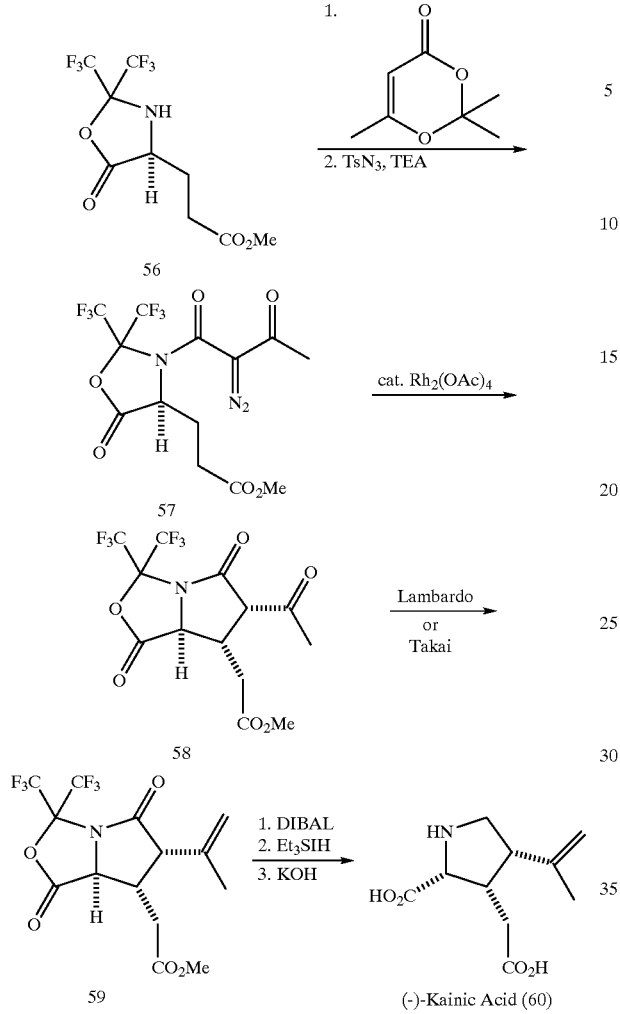

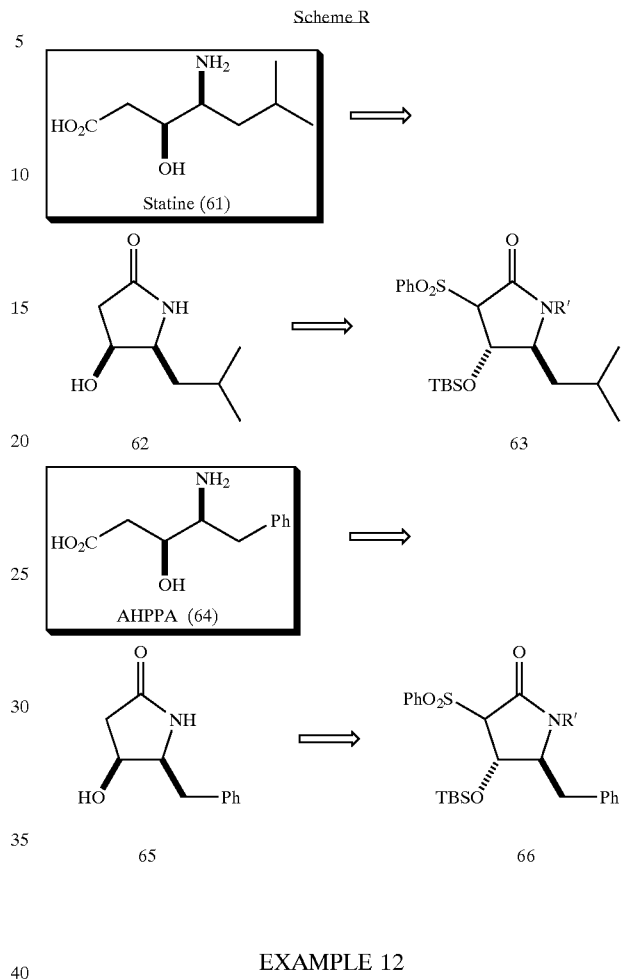

Selective methylenation gives rise to the formation of olefin 59. The amide is reduced selectively using the reported two step sequence (Mateo, A. I. & Rubio, A. "Stereocontrolled Synthesis of 4-Substituted Kanaic Acid" 1998, J. Org. Chem. 63:1995), then the subsequent hydrolysis secures the natural product 60.

EXAMPLE 11

Synthesis of Statine and AHPPA by Method C

Statine (61) is a nonprotein organic compound, which constitutes a key component of the naturally occurring peptidic aspartate protease inhibitor pepstatin. The potential inhibitory activity of pepstatin and its structural analogs, especially AHPPA, towards the aspartate proteases prompted synthetic efforts.

These simple chiral compounds can be derived from the γ-lactams prepared via method C (acyclic substrates). As retrosynthetically illustrated below, statine and AHPPA are synthesized from γ-lactams, starting from leucine and phenylalanine, respectively. Appropriate deprotection of masking groups delivers lactams 62 and 65, which are transformed to the natural products by hydrolysis. Although there are more synthetic steps in these syntheses than simply an efficient asymmetric arninohydroxylation, this route secures optical purity, and the intermediates allow a variety of highly functionalized analogs.

EXAMPLE 12

Synthesis of Rolipram and Epolactaene by Method D

This example illustrates the synthesis of two pharmaceutically important compounds, rolipram and epolactaene, utilizing method D. Rolipram is an antidepressant and a potent inhibitor of phosphodiesterase type IV.

As delineated below, the synthesis of rolipram requires 10 linear steps via the chiral auxiliary 26. Aldehyde 67 is derived from isovanillin, which is then subjected to the coupling with 26 to acquire 68. The syn diastereomer is obtained exclusively. Oxidation followed by diazo transfer affords the C—H insertion precursor 69. Cyclization leads to the stereoselective synthesis of the bicyclic lactam 70, which is converted to rolipram 71 via sequential defunctionalizations.

Scheme S

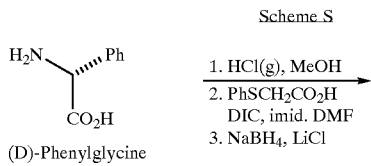

(D)-Phenylglycine

1. HCl(g), MeOH
2. PhSCH₂CO₂H DIC, imid. DMF
3. NaBH₄, LiCl

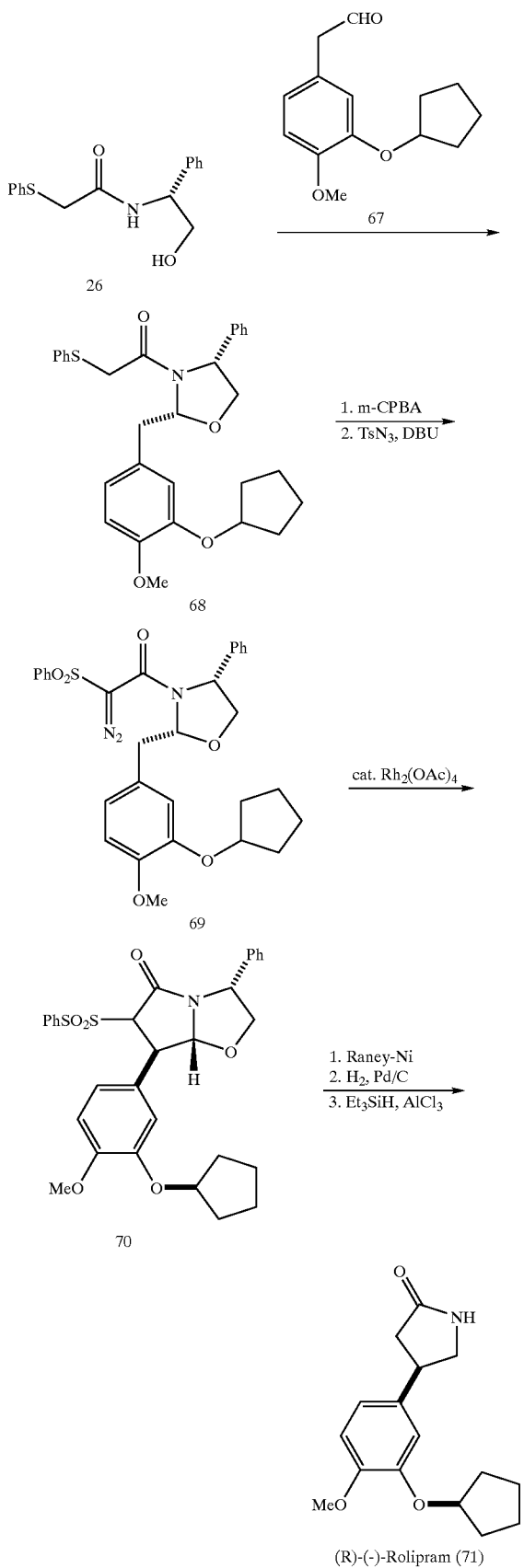

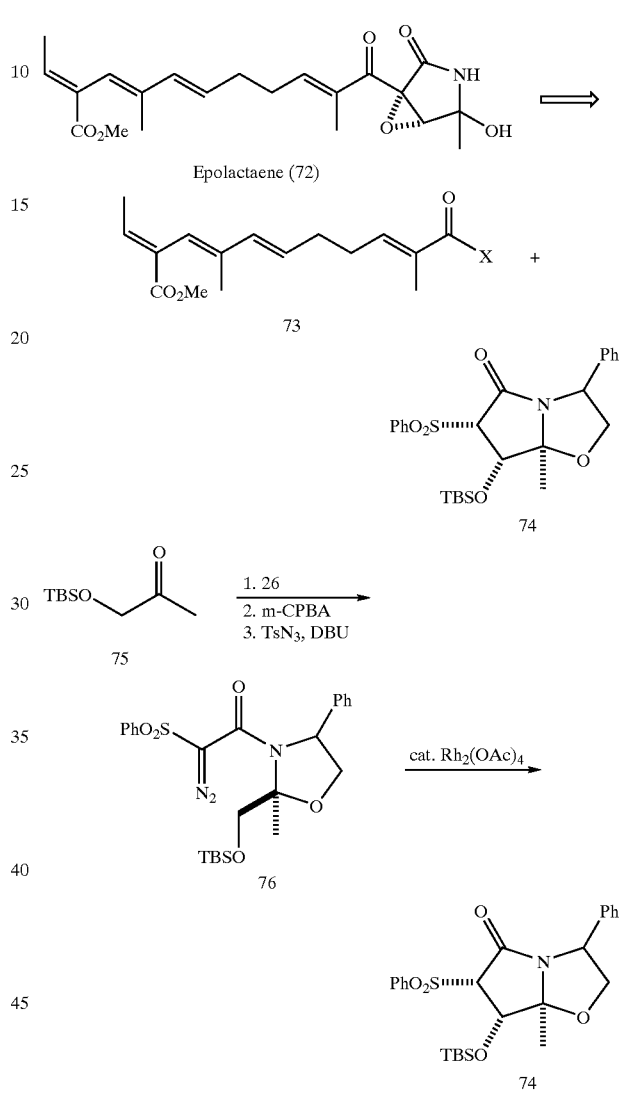

Likewise, epolactaene 72 is prepared using the known synthetic pathways as illustrated retrosynthetically in Scheme T. Synthetic intermediate 74 is a good coupling partner with the known side chain 73. Synthesis of cyclization product 74 utilizes method D.

After ketone 75 and chiral template 26 are coupled, oxidation and diazo transfer yields 76. Intramolecular C—H insertion smoothly yields the bicyclic compound 74, which is conjugated with 73.

Certain patents and printed publications are referred to herein. All such patents and printed publications are herein incorporated by reference in their respective entireties.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method of synthesizing a structure compound of formula (II) said method comprising:
providing a compound of formula (I),

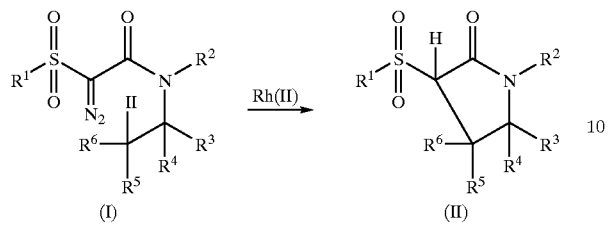

in which:

R$_1$, R$_4$, R$_5$, and R$_6$, are independently H, halo, N$_3$, CN, NC, (C$_1$–C$_{22}$)alkyl, (C$_6$–C$_{10}$)aryl, (C$_3$–C$_8$)cycloalkyl, (C$_7$–C$_{32}$)aralkyl, (C$_7$–C$_{32}$)alkylaryl, OR, SR, N(R)$_2$, CO$_2$R, C(O)R, P(O)(OR)$_2$, COR, CF$_3$, S(O)R, or SO$_2$R, wherein each R is independently H, (C$_{1-C22}$)alkyl, (C$_{6-C10}$)aryl, (C$_{3-C8}$)cycloalkyl, (C$_2$–C$_{22}$)alkenyl, (C$_5$–C$_8$)cycloalkenyl, (C$_7$–C$_{32}$)aralkyl, (C$_7$–C$_{32}$)alkylaryl, C$_9$–C$_{32}$)aralkenyl, or (C$_9$–C$_{32}$)alkenylaryl, and R$_2$ and R$_3$ together comprise —C(CH$_3$)$_2$—O—CH$_2$—, —(CH$_2$)$_n$—O—C(O)—, or —C(X)—O—CH$_2$— where n=0–10, and X is (C$_6$–C$_{10}$)aryl or (C$_7$–C$_{32}$)alkylaryl; or R$_2$ and R$_3$ are independently H, halo, N$_3$, CN, NC, (C$_1$–C$_{22}$)alkyl, (C$_6$–C$_{10}$)aryl, (C$_3$–C$_8$)cycloalkyl, (C$_2$–C$_{22}$)alkenyl, (C$_5$–C$_8$)cycloalkenyl, (C$_7$–C$_{32}$)aralkyl, (C$_7$–C$_{32}$)alkylaryl, (C$_9$–C$_{32}$)aralkenyl, (C$_9$–C$_{32}$)alkenylaryl, OR, SR, N(R)$_2$, NH(R), CO$_2$R, C(O)R, P(O)(OR)$_2$, COR, CF$_3$, S(O)R, or SO$_2$R, wherein each R is independently H, (C$_1$–C$_{22}$)alkyl, (C$_6$–C$_{10}$)aryl, (C$_3$–C$_8$)cycloalkyl, (C$_2$–C$_{22}$)alkenyl, (C$_5$–C$_8$)cycloalkenyl, (C$_7$–C$_{32}$)aralkyl, (C$_7$–C$_{32}$)alkylaryl, (C$_9$–C$_{32}$)aralkenyl, or (C$_9$–C$_{32}$)alkenylaryl; and reacting said compound of formula (I) under conditions promoting intramolecular C—H insertion, whereby said lactam or said pyrrolidinone precursor compound of formula (II) is synthesized.

2. The method of claim 1, in which R$_1$ is phenyl.

3. The method of claim 1, in which R$_2$ and R$_3$ together comprise —C(CH$_3$)$_2$—O—CH$_2$—.

4. The method of claim 1, in which R$_2$ and R$_3$ together comprise —CH$_2$—O—C(O)—.

5. The method of claim 1, in which R$_2$ and R$_3$ together comprise —C(—Y—X)—CH$_2$—O—, where —Y—X is (C$_6$–C$_{10}$)aryl.

6. The method of claim 1, in which said conditions promoting intramolecular C—H insertion compromise the addition of an effective amount of rhodium salt.

7. The method of claim 1 in which said rhodium salt is Rh$_2$(OAc)$_4$.

* * * * *

UNITED STATES PATENT AND TRADEMARK OFFICE
CERTIFICATE OF CORRECTION

PATENT NO.    : 6,689,890 B2
DATED         : February 10, 2004
INVENTOR(S)   : Kyung Woon Jung and Cheol Hwan Yoon It is certified that error appears in the above-identified patent and that said Letters Patent is hereby corrected as shown below:

Column 5,
Line 66, "Where $R_1$, R4, $R_5$, and R6 are, for example," should read -- Where $R_1$, $R_4$, $R_5$, and $R_6$ are, for example, --

Column 6,
Lines 13 and 14, "...structure in which R2 and R3 together comprise..." should read -- ...structure in which $R_2$ and $R_3$ together comprise... --.
Line 53, "...originally substitute; or $R^2$ and $R^3$ when taken..." should read -- originally substituted; or $R_2$ and $R_3$ when taken --
Line 64, "$R^3$ and $R^4$ when connected to each other, form 4- to..." should read -- $R_3$ and $R_4$ when connected to each other, form 4- to... --

Column 7,
Line 1, "$R^4$ and $R^5$ when connected to each other, form 4- to..." should read -- $R_4$ and $R_5$ when connected to each other, form 4- to... --
Line 5, "$R^5$ and $R^6$ when connected to each other, form 4- to..." should read -- $R_5$ and $R_6$ when connected to each other, form 4- to... --

Column 8,
Line 49, "...OC(=O)NR2." should read -- OC(=O)$NR_2$. --.

Column 11,
Lines 56-64, "...allyl..." should read -- ...alkyl... --

Column 13,
Line 5, "...allyl..." should read -- ...alkyl... --

Column 19,
Line 53, "...α-phenylsulfonylacetamide III4." should read -- ...α-phenylsulfonylacetamide III-4. --.

Column 24,
Line 14, "Structure labeled '24" should read -- structure not labeled "24" --.

Column 27,
Line 51, "α-phenylsulfonylacetamide XI4 is obtained from..." should read -- α-phenylsulfonylacetamide XI-4 is obtained from... --.

Column 29,
Line 2, "...3.41 (m, 1 HZ, 4.27 (m, 1H)," should read -- ...3.41 (m, 1H), 4.27 (m, 1H), --
Lines 65 and 66, "...3.89 (ddd, 1H), J=5.5," should read -- ...3.89 (ddd, 1H, J=5.5, --.

UNITED STATES PATENT AND TRADEMARK OFFICE
CERTIFICATE OF CORRECTION

PATENT NO. : 6,689,890 B2
DATED : February 10, 2004
INVENTOR(S) : Kyung Woon Jung and Cheol Hwan Yoon It is certified that error appears in the above-identified patent and that said Letters Patent is hereby corrected as shown below:

Column 30,
Line 21, "Following the procedure of the preparation of XI-1," should read -- Following the procedure of the preperation of XII-1, --.

Column 31,
Lines 35-40, 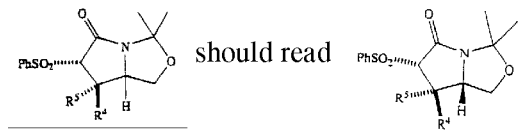 should read

Column 34,
Structure No. 46, 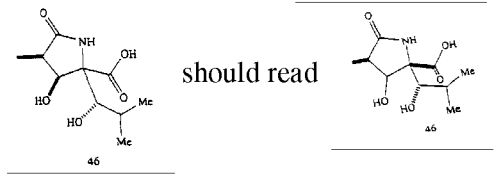 should read 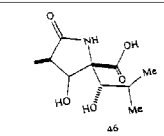

Column 37,
Line 67, "...asymmetric arninohydroxylation," should read -- ...asymmetric aminohydroxylation, --.

Column 40,
Structure No. 74, 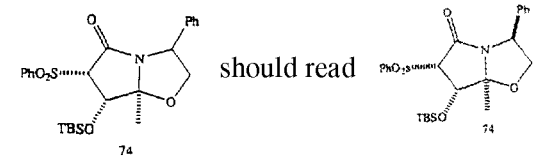 should read 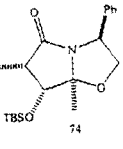

Structure No. 76, 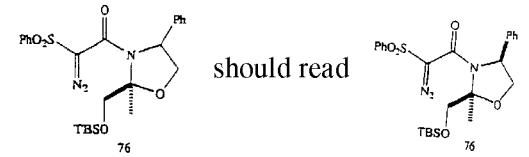 should read 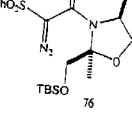

Column 41,
Structure No. I, 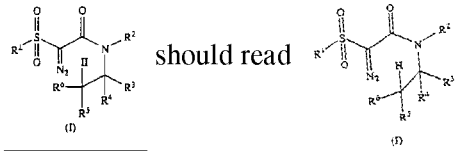 should read 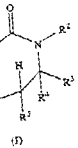

Lines 1 and 2, "1. A method of synthesizing a structure compound of formula (II) said method comprising:" should read -- 1. A method of synthesizing a compound of formula (II) said method comprising: --.
Lines 21 and 22, "...($C_{1-C22}$)alkyl, ($C_{6-C10}$)aryl, ($C_{3-C8}$)cycloalkyl," should read -- ...($C_1$-$C_{22}$)alkyl, ($C_6$-$C_{10}$)aryl, ($C_3$-$C_8$)cycloalkyl. --.

UNITED STATES PATENT AND TRADEMARK OFFICE
CERTIFICATE OF CORRECTION

PATENT NO.     : 6,689,890 B2
DATED          : February 10, 2004
INVENTOR(S)    : Kyung Woon Jung and Cheol Hwan Yoon It is certified that error appears in the above-identified patent and that said Letters Patent is hereby corrected as shown below:

Column 42,
Line 13, "...said lactam or said pyrrolidinone precursor compound of formula (II) is synthesized." should read, -- said compound of formula (II) is synthesized. --.
Line 20, "5. The method of claim 1, in which $R_2$ and $R_3$ together comprise $-C-Y-X)-CH_2-O-$, where $-Y-X$ is $(C_6-C_{10})$aryl." should read, -- 5. The method of claim 1, in which $R_2$ and $R_3$ together comprises $-C(X)-CH_2-O-$, where X is $(C_6-C_{10})$aryl. --.

Signed and Sealed this

Twenty-first Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,689,890 B2
APPLICATION NO. : 10/323537
DATED : February 10, 2004
INVENTOR(S) : Kyung Woon Jung and Cheol Hwan Yoon It is certified that error appears in the above-identified patent and that said Letters Patent is hereby corrected as shown below:

Column 1,
Line 5, "This application is a continuation-in-part application filed from U.S. Ser. No. 09/848,268; filed May 4, 2001 now abandoned and claims the benefit of provisional patent application Serial No. 60/201,734; filed May 4, 2000, which is incorporated by reference herein in its entirely, including any figures, table, or drawings.

Should read --This application is a continuation-in-part application filed from U.S. Ser. No. 09/848,268; filed May 4, 2001 now abandoned and claims the benefit of provisional patent application Serial No. 60/201,734; filed May 4, 2000, which is incorporated by reference herein in its entirely, including any figures, table, or drawings.--.

Col. 1 lines 29-30 should read --This invention was made with government support under GM62767 awarded by National Institutes of Health. The government has certain rights in the invention.--.

Signed and Sealed this

Thirteenth Day of May, 2008

JON W. DUDAS
*Director of the United States Patent and Trademark Office*